(12) United States Patent
Perez et al.

(10) Patent No.: US 12,369,898 B2
(45) Date of Patent: Jul. 29, 2025

(54) CIRCUMFERENTIAL RETRACTOR SYSTEM

(71) Applicant: Applied Medical Resources Corporation, Rancho Santa Margarita, CA (US)

(72) Inventors: Deryk Perez, Rancho Santa Margarita, CA (US); Daniel Astudillo, Capistrano Beach, CA (US); Joel Velasco, Rancho Santa Margarita, CA (US); Sofie Wright, Rancho Santa Margarita, CA (US); Serene Wachli, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 258 days.

(21) Appl. No.: 18/319,974

(22) Filed: May 18, 2023

(65) Prior Publication Data
US 2023/0363752 A1    Nov. 16, 2023

Related U.S. Application Data

(63) Continuation of application No. PCT/US2022/017887, filed on Feb. 25, 2022.

(60) Provisional application No. 63/154,290, filed on Feb. 26, 2021, provisional application No. 63/154,227, filed on Feb. 26, 2021.

(51) Int. Cl.
*A61B 17/02* (2006.01)
*A61B 17/34* (2006.01)

(52) U.S. Cl.
CPC ...... *A61B 17/0218* (2013.01); *A61B 17/0281* (2013.01); *A61B 17/3423* (2013.01); *A61B 2017/0225* (2013.01)

(58) Field of Classification Search
CPC ............... A61B 17/02; A61B 17/0218; A61B 2017/0225; A61B 17/0281; A61B 17/0293; A61B 17/3423; A61B 17/3462; A61B 2017/3466; A61B 17/42
See application file for complete search history.

(56) References Cited

U.S. PATENT DOCUMENTS 8,357,085 B2 * 1/2013 Shelton, IV ....... A61B 17/3423
                                                         600/203
8,668,641 B2 * 3/2014 Smith ................ A61B 17/3423
                                                         600/203

(Continued)

FOREIGN PATENT DOCUMENTS

EP     2 644 137 A2       10/2013
WO    WO 03/103548 A1     12/2003
WO    WO 2016/028789 A2    2/2016

OTHER PUBLICATIONS

European Patent Office, The International Search Report and Written Opinion for International Application No. PCT/US2022/017887, entitled "Circumferential Retractor System," mailed Aug. 12, 2022, 20 pgs.

(Continued)

*Primary Examiner* — Larry E Waggle, Jr.
(74) *Attorney, Agent, or Firm* — Patrick Ikehara

(57) ABSTRACT

A circumferential retractor system is provided that includes a circumferential retractor and a flexible retainer. The circumferential retractor and retainer retracts and protects a patient's body opening, providing access into a patient.

20 Claims, 21 Drawing Sheets

(56) References Cited

U.S. PATENT DOCUMENTS

| | | | | |
|---|---|---|---|---|
| 8,845,529 B2* | 9/2014 | Smith | ............... | A61B 17/3431 |
| | | | | 600/207 |
| 9,017,249 B2* | 4/2015 | Smith | ............... | A61M 39/0247 |
| | | | | 600/204 |

OTHER PUBLICATIONS

European Patent Office, The International Search Report and Written Opinion for International Application No. PCT/US2022/017887, entitled "Circumferential Retractor System," mailed Aug. 19, 2022, 20 pgs.

The International Bureau of WIPO, International Preliminary Report on Patentability for International Application No. PCT/US2022/017887, entitled "Circumferential Retractor System," dated Sep. 7, 2023, 13 pgs.

* cited by examiner

CIRCUMFERENTIAL RETRACTOR SYSTEM

CROSS-REFERENCE TO RELATED APPLICATIONS

This is a continuation of International Application No. PCT/US2022/17887, filed on Feb. 25, 2022, which claims priority to and benefit of U.S. Provisional Patent Application Serial Nos. 63/154,227, filed on Feb. 26, 2021 and 63/154,290, filed on Feb. 26, 2021, all the disclosures of which are incorporated herein by reference in their entirety.

BACKGROUND

The present application is generally directed to surgical access devices and more particularly to circumferential protector and/or retractor systems and methods for surgical procedures operating within a body cavity or through an opening or orifice.

Working space inside the body cavity is always limited, especially when using surgical instruments and devices. Some procedures require placement of such instruments through very small incisions or openings into relatively small body cavities or surgical spaces, often with poor or limited visibility. Small retractors in such limited space procedures can maintain or support small incisions or openings but also provides reduced instrument triangulation for users compared to larger retractors, limiting their usefulness.

SUMMARY

In accordance with various embodiments, a circumferential protector/retractor is provided. In accordance with various embodiments, a circumferential retractor system comprises a circumferential protector/retractor and a retainer. In various embodiments, the circumferential retractor comprises an outer ring having an outer diameter and arranged to be placed outside of a body cavity, an inner ring having an outer diameter and arranged to be placed inside of the body cavity, and a sheath. In various embodiments, the sheath comprises an upper segment connected to the outer ring and having a cylindrical shape with a proximal end having an inner diameter matching or smaller than the outer diameter of the outer ring and a distal end having an inner diameter matching or smaller than the outer diameter of the outer ring. In various embodiments, the sheath further comprises a lower segment connected the inner ring with the lower segment having a frustoconical shape with a proximal end having an inner diameter matching or smaller than the outer diameter of the outer ring and a distal end having an inner diameter smaller than or matching the outer diameter of the inner ring and smaller than the outer diameter of the outer ring. The sheath delimits an access channel extending from the outer ring to the inner ring. In various embodiments, the retainer is a monolithic hourglass shaped flexible retainer being positioned outside of the access channel and arranged to surround and be in contact with a distal portion of the lower segment of the sheath.

In various embodiments, the upper and lower segments of the sheath are made from the same material and form a monolithic structure. In various embodiments, the proximal end of the upper segment of the sheath is arranged to be placed outside the body cavity and the distal end of the upper segment of the sheath is arranged to be placed inside the body cavity. In various embodiments, the upper segment has a shape or profile matching an outer profile of the outer ring and/or has an adjustable length arranged to apply a radial force with the adjustment of the length of the upper segment. In various embodiments, the length of the upper segment is adjustable by the outer ring being rolled or rotated and wrapping portions of the upper segment around the outer ring while the lower segment remains unchanged. In various embodiments, the outer ring is prevented from being rotated, rolled and/or adjusted passed a predetermined stop position between the upper and lower segments of the sheath. In various embodiments, the sheath comprises an indicator marking the predetermined stop position between the upper and lower segments of the sheath for the outer ring or a predetermined position between the upper and lower segments of the sheath.

In various embodiments, a length of the upper segment is adjustable and a length of the lower segment is not adjustable and wherein the lower segment connected to the inner ring is not separable from the inner ring and/or the upper segment connected to the outer ring is not separable from the outer ring. In various embodiments, the sheath is compressible and/or made of a non-metallic material. In various embodiments, the inner ring is compressible from a circular shape into an oblong shape and/or biased to return to the circular shape and/or the outer ring is not compressible. In various embodiments, the retainer has a length less than an overall length of the sheath, is compressible and/or has a non-adjustable length. In various embodiments, the lower segment of the sheath conforms to a shape, e.g., an hourglass shape, of the retainer.

In various embodiments, the retainer is arranged to be placed between the sheath and tissue and/or the lower segment of the sheath is arranged to be placed between the retainer and inserted instruments. In various embodiments, the retainer is arranged to surround only the lower segment of the sheath and/or an outer surface of the lower segment of the sheath is disposed between an inner surface of the lower segment and an inner surface of the retainer. In various embodiments, the retainer is more flexible than the outer ring and/or the inner ring and/or is less flexible than the sheath. In various embodiments, the retainer is disposed between the upper segment and the inner ring and/or the sheath is arranged to enlarge a central opening of the retainer. In various embodiments, the sheath is arranged to straighten or flatten out the retainer. In various embodiments, the sheath is arranged to straighten or flatten out a middle portion of the hourglass shape of the retainer. In various embodiments, the sheath is arranged to deform the shape of the retainer, e.g., an hourglass shape, to a different shape, e.g., a cylindrical shape. In various embodiments, the sheath is arranged to straighten, flatten and/or deform the retainer when and/or due to shortening and/or adjusting the length of the upper segment of the sheath. In various embodiments, the retainer has a non-adjustable length and/or an upper inner diameter smaller than an inner diameter of the outer ring and/or a middle inner diameter smaller than the upper inner diameter and smaller than an inner diameter of the outer ring. In various embodiments, the retainer is temporarily deformable by a user and/or has an initial shape and being deformable and biased to return to its initial shape.

In various embodiments, the outer ring comprises a flexible ring having a lumen and a curved rod disposed within the lumen of the flexible ring, the curved rod being more rigid than the flexible ring. In various embodiments, the outer ring is rotatable about itself. In various embodiments, a length of the lower segment is longer than a length of the upper segment, the length of the upper segment being less than half an overall length of the sheath and/or the length of the lower segment being greater than half the overall length of the sheath. In various embodiments, the lower segment has an upper diameter proximal to the upper segment and a lower diameter proximal to the inner ring, the lower diameter of the lower segment being smaller than the upper diameter of the lower segment, and/or the outer diameter of the outer ring is greater than the outer diameter of the inner ring.

In various embodiments, a distal section of the retainer has a distal lip at its distal end to facilitate securement of the distal section to the inside of the body cavity and/or a proximal section of the retainer has a proximal lip at its proximal end to facilitate securement of the proximal section to the outside of the body cavity. In various embodiments, a distal section of the retainer has an outer diameter greater than an outer diameter of the inner ring and/or a proximal section of the retainer has an inner diameter greater than an outer diameter of the inner ring and/or an inner diameter of the retainer between the proximal section and the distal section of the retainer is smaller than an inner diameter of the inner ring. In various embodiments, a sealing cap is arranged to connect to the outer ring and/or portions of the upper segment of the sheath. In various embodiments, the sealing cap seals the access channel and/or a connection between the sealing cap, the outer ring, and/or a portion of the upper segment. In various embodiments, a tether attached to the inner ring and/or the tether has a length greater than an overall length of the sheath and/or has a tether tag attached to the tether.

In accordance with various embodiments, a circumferential protector/retractor comprises a sheath comprising an upper segment having a first shape and a lower segment having a second shape different from the first shape of the upper segment. In various embodiments, a retainer has a third shape different from the first shape of the upper segment and the second shape of the lower segment.

In various embodiments, the retainer has a length greater than a length of the upper segment, has a length less than an overall length of the sheath, and/or has a non-adjustable length. In various embodiments, the retainer is compressible, arranged to be placed between the sheath and tissue, and/or is arranged to only surround the lower segment of the sheath. In various embodiments, an outer surface of the lower segment of the sheath is disposed between an inner surface of the lower segment and an inner surface of the retainer and/or the sheath is arranged to enlarge a central opening of the retainer. In various embodiments, the sheath is arranged to straighten or flatten out the retainer. In various embodiments, the sheath is arranged to deform the shape of the retainer to a different shape. In various embodiments, the sheath is arranged to straighten, flatten and/or deform the retainer when and/or due to shortening and/or adjusting the length of the upper segment of the sheath. In various embodiments, the retainer is less flexible than the sheath, is not adjustable, has a non-adjustable length, is elastic, is temporarily deformable by a user, is deformable into a fourth shape different from the third shape and biased to return to the third shape, and/or is more rigid than the sheath.

In various embodiments, a circumferential retractor system comprises a circumferential protector/retractor comprising a sheath comprising an upper segment having a first shape and a lower segment having a second shape different from the first shape of the upper segment. In various embodiments, the upper and lower segments of the sheath are made from the same material and/or form a monolithic structure. In various embodiments, a proximal portion of the upper segment of the sheath is arranged to be placed outside a body wall and/or a distal portion of the upper segment of the sheath is arranged to be placed inside the body wall.

In various embodiments, the length of the lower segment is longer than the length of the upper segment, the length of the upper segment is less than half an overall length of the sheath, and/or the length of the lower segment is less than half an overall length of the sheath. In various embodiments, the length of the upper segment is adjustable and/or the length of the lower segment is not adjustable. In various embodiments, the sheath is compressible, made of a non-metallic material, is multi-layered or any combination thereof. In various embodiments, an outer ring is connected to the upper segment of the sheath and/or an inner ring is connected to the lower segment of the sheath. In various embodiments, the first shape of the upper segment matches and/or has an outer profile matching an outer profile of an outer ring connected to the upper segment. In various embodiments, the upper segment is arranged to apply a radial force as the upper segment is shorten, has an adjustable length arranged to apply a radial force with the adjustment of the length of the upper segment, and/or is adjustable by the outer ring being rolled, rotated and/or adjusted, gathering and/or wrapping the upper segment around the outer ring while the lower segment and/or its length remains unchanged. In various embodiments, the upper segment is arranged to apply a radial force as the upper segment is shorten by the outer ring being rotated about itself wrapping portions of the upper segment around the outer ring while a length of the lower segment remains unchanged.

In various embodiments, the outer ring is prevented from being rotated and/or adjusted passed a predetermined position on the sheath, the upper or lower segments, the distal end of the upper segment and/or the proximal end of the lower segment. In various embodiments, the outer ring has a diameter that is fixed and non-adjustable. In various embodiments, the outer ring comprises a plurality of rings, a first ring stacked on a second ring, a flexible ring and a rigid ring less flexible than the flexible ring, and/or a flexible ring having a lumen and a curved rigid rod, hoop or bar disposed within the lumen of the flexible ring.

In various embodiments, the outer ring comprises an internal rigid ring encased in an external flexible ring, the internal rigid ring being more rigid than the external flexible ring. In various embodiments, the internal rigid ring is made of metal and/or the external flexible ring is made of plastic. In various embodiments, the internal rigid ring is made of material with a hardness greater than a material of the external flexible ring. In various embodiments, the outer ring is rotatable around itself. In various embodiments, the outer ring has a fixed predetermined diameter, has a fixed thickness about or less than one sixth ($\frac{1}{6}$) of an overall length of the upper segment, and/or has a fixed height about or less than one sixth ($\frac{1}{6}$) of an overall length of the upper segment.

In various embodiments, the inner ring comprises a slit facilitating folding of the inner ring, is compressible into an oblong shape, is deformable placing inner portions of the inner ring in contact with each other, is returnable back to its initial shape, and/or is biased to return to its initial shape. In various embodiments, the inner ring has a fixed circumference that cannot be enlarged. In various embodiments, the inner ring is deformable and/or the outer ring is not deformable. In various embodiments, the inner ring is a distalmost portion of the circumferential retractor. In various embodiments, a sealing cap is arranged to connect to the outer ring and/or portions of the upper segment of the sheath and/or a tether attached to the inner ring. In various embodiments, the tether has a length greater than an overall length of the sheath and/or a tether tag attached to the tether.

In various embodiments, a distal end of the lower segment of the sheath is connected to an inner portion of the inner ring. In various embodiments, a distal end of the lower segment of the sheath is connected to an outer portion of the inner ring. In various embodiments, the lower segment of the sheath is tapered. In various embodiments, the second shape of the lower segment of the sheath is a truncated conical shape tapering from a distal end of the upper segment to the inner ring. In various embodiments, the lower segment has a diameter progressively decreasing from a proximal end of the lower segment to a distal end of the lower segment. In various embodiments, the lower segment has a diameter progressively decreasing at a constant rate from a proximal end of the lower segment to a distal end of the lower segment. In various embodiments, the lower segment has curved side walls. In various embodiments, the lower segment has symmetrical side walls. In various embodiments, the lower segment has curved symmetrical side walls.

In various embodiments, the upper segment has a constant outer and a constant inner diameter extending from a proximal end of the upper segment to a distal end of the upper segment. In various embodiments, the constant outer and/or inner diameter of the upper segment reduces sheath tension by maintaining a sheath diameter that matches a diameter of the outer ring with each flip, rotation, or adjustment of the outer ring. In various embodiments, the upper segment has a lower or smaller sheath tension than the lower segment. In various embodiments, the lower segment has a greater sheath tension than the upper segment. In various embodiments, the upper segment is arranged to be wound, wrapped and/or rotated around the outer ring a predetermined number of times. In various embodiments, the predetermined number of times is at least six and/or about six and/or less.

In various embodiments, the lower segment has a sidewall extending in a direction transverse, perpendicular and/or lateral to a longitudinal axis of the sheath. In various embodiments, the upper segment has a sidewall extending in a direction parallel to a longitudinal axis of the sheath. In various embodiments, portions of the lower segment are angled relative to the upper segment. In various embodiments, the shape, e.g., a third shape, of the retainer has a proximal funnel and/or an opposing distal funnel. In various embodiments, the retainer has a proximal funnel or taper section and/or an opposing distal funnel or taper section. In various embodiments, the proximal funnel section from its proximal end has a progressively decreasing diameter to its distal end. In various embodiments, the distal funnel section from its proximal end has a progressively increasing diameter to its distal end. In various embodiments, the retainer has an hourglass shape.

In various embodiments, a sheath comprises an upper segment connected to an outer ring and being unable to separate from the outer ring. In various embodiments, an upper segment of a sheath has a substantially cylindrical shape. In various embodiments, an upper segment of a sheath has a proximal end having an outer diameter equal or greater than an inner diameter of an outer ring connected to the sheath but less than or equal to the outer diameter of the outer ring. In various embodiments, an upper segment of a sheath has a distal end having an outer diameter equal to an outer diameter of a proximal end of the upper segment of the sheath. In various embodiments, an upper segment of a sheath has a constant inner and/or outer diameter throughout an entire length of the upper segment of the sheath. In various embodiments, the sheath comprises a lower segment connected to and unable to separate from an inner ring. In various embodiments, a lower segment of a sheath has a substantially frustoconical shape. In various embodiments, a lower segment of a sheath has a constant progressively decreasing inner and/or outer diameter throughout an entire length of the lower segment of the sheath. In various embodiments, a lower segment of a sheath has a proximal end having an outer diameter equal to an outer diameter of a proximal end of an upper segment of a sheath. In various embodiments, a lower segment of a sheath has a distal end having an inner diameter equal to or smaller than an outer diameter of an inner ring and smaller than an outer diameter of an outer ring. In various embodiments, a sheath comprises a lumen extending from an upper segment through a lower segment and delimits an access channel extending through the lumen from an outer ring to an inner ring. In various embodiments, a sheath comprises upper and lower segments being formed as a monolithic structure and having differing lengths from each other. In various embodiments, a monolithic hourglass shaped retainer is provided. In various embodiments, a retainer is positioned outside of an access channel and a lumen of a sheath. In various embodiments, a retainer is arranged to surround and be in contact with a lower segment of a sheath. In various embodiments, a retainer is disposed between an upper segment and an inner ring. In various embodiments, an outer surface of a lower segment of a sheath is disposed between an inner surface of the lower segment of the sheath and an inner surface of a retainer. In various embodiments, an inner ring is arranged to be inserted through a central opening of a retainer and able to be positioned near a distal end of the retainer. In various embodiments, a sheath is arranged to enlarge a central opening of a retainer.

In various embodiments, an upper segment of a sheath has a proximal portion arranged to be placed outside a body wall and a distal portion arranged to be placed inside the body wall. In various embodiments, an inner ring is a distalmost portion of the circumferential retractor. In various embodiments, a sealing cap is arranged to connect to an outer ring and proximal portions of an upper segment of a sheath. In various embodiments, a tether is attached to an inner ring. In various embodiments, a tether tag is attached to a tether. In various embodiments, a tether has a length greater than an overall length of a sheath. In various embodiments, a tether is arranged to move an inner ring away from a distal end of a retainer towards a central opening of the retainer as the tether is moved proximally.

In various embodiments, a retainer has a non-adjustable length. In various embodiments, a retainer has a length greater than a length of an upper segment of a sheath. In various embodiments, a retainer has a length less than an overall length of the sheath. In various embodiments, a retainer is deformable by a user into a shape different from an hourglass shape and biased to return to the hourglass shape. In various embodiments, a retainer is arranged to be placed between a sheath and tissue.

In accordance with various embodiments, a circumferential retractor system is provided comprising a first circumferential retractor, a retainer and/or a second circumferential retractor. In various embodiments, the first circumferential retractor comprises a sheath comprising an upper segment having a first shape and a lower segment having a second shape different from the first shape of the upper segment. In various embodiments, the retainer is disposed between the first circumferential retractor and the second circumferential retractor. In various embodiments, the retainer is more rigid than the upper segment and the lower segment of the sheath. In various embodiments, the upper segment has an adjustable length, the retainer has a fixed and non-adjustable length and/or the lower segment has a fixed and non-adjustable length.

In various embodiments, an inner ring is connected to and/or inseparable from the lower segment of the first circumferential retractor and/or the inner ring is arranged to be inserted through a central opening of the retainer. In various embodiments, the inner ring is arranged to be positioned distally and/or positioned near a distal end of the retainer. In various embodiments, an outer ring is connected to the upper segment and/or is inseparable from the upper segment. In various embodiments, the outer ring has a first position distal from a proximal end of the retainer and a second position proximate to the proximal end of the retainer and, in various embodiments, the outer ring is rotatable to move the outer ring from the first position to the second position. In various embodiments, the sheath is arranged to secure the retainer between the lower segment of the sheath and the inner ring. In various embodiments, the upper segment has an adjustable length arranged to secure the retainer between the lower segment of the sheath and the inner ring. In various embodiments, the sheath comprises a protrusion arranged to secure the retainer between the protrusion and the inner ring.

In various embodiments, the second circumferential retractor comprises and/or is a containment bag. In various embodiments, the second circumferential retractor comprises a sheath having a cylindrical shape, a containment bag, and/or a truncated conical shape. In various embodiments, the second circumferential retractor has a portion, e.g., a distal portion, arranged to be inserted through and positioned within a body wall, the retainer being arranged to be inserted through and positioned within the body wall and on top of the portion, e.g., the distal portion, of the second circumferential retractor, and/or the lower segment of the first circumferential retractor arranged to be inserted through and positioned within the body wall and on top of the retainer.

In various embodiments, the sheath is arranged to secure the retainer between the lower segment of the sheath and the inner ring. In various embodiments, the upper segment has an adjustable length arranged to secure the retainer between the lower segment of the sheath and the inner ring. In various embodiments, the sheath comprises a protrusion arranged to secure the retainer between the protrusion and the inner ring. In various embodiments, the protrusion extends circumferentially, fully or partially, around the sheath. In various embodiments, the protrusion has a width or height smaller than a width or height of the inner ring. In various embodiments, the circumferential retractor comprises a containment bag. In various embodiments, the sheath has a cylindrical shape, a containment bag, and/or a truncated conical shape.

In various embodiments, a circumferential retractor system is provided comprising a circumferential retractor and/or a retainer. In various embodiments, a circumferential retractor comprises an outer ring having an outer diameter and arranged to be placed outside of a body cavity, an inner ring having an outer diameter and arranged to be placed inside of the body cavity, and a sheath. In various embodiments, the sheath comprises an upper segment connected to the outer ring, the upper segment having a cylindrical shape with a proximal end having an outer diameter matching an inner diameter of the outer ring and a distal end having an outer diameter matching the inner diameter of the outer ring, the outer ring being inseparable from the upper segment, and a lower segment connected to and inseparable from the inner ring, the lower segment having a frustoconical shape with a proximal end having an outer diameter matching the inner diameter of the outer ring and a distal end having an inner diameter matching or smaller than the outer diameter of the inner ring and smaller than the outer diameter of the outer ring, the sheath having a lumen extending from the upper segment through the lower segment and delimiting an access channel extending through the lumen from the outer ring to the inner ring, and the upper and lower segments being formed as a monolithic structure and having differing lengths. In various embodiments, the retainer comprises a monolithic hourglass shaped retainer being positioned outside of the access channel and the lumen of the sheath, arranged to surround and be in contact with a distal portion of the lower segment of the sheath, and is disposed between the upper segment and the inner ring, and wherein an outer surface of the lower segment of the sheath is disposed between an inner surface of the lower segment and an inner surface of the retainer, the inner ring being arranged to be inserted through a central opening of the retainer and positioned near a distal end of the retainer and the sheath being arranged to enlarge the central opening of the retainer.

Many of the attendant features of the present inventions will be more readily appreciated as the same becomes better understood by reference to the foregoing and following description and considered in connection with the accompanying drawings.

DETAILED DESCRIPTION

Figure 1A:
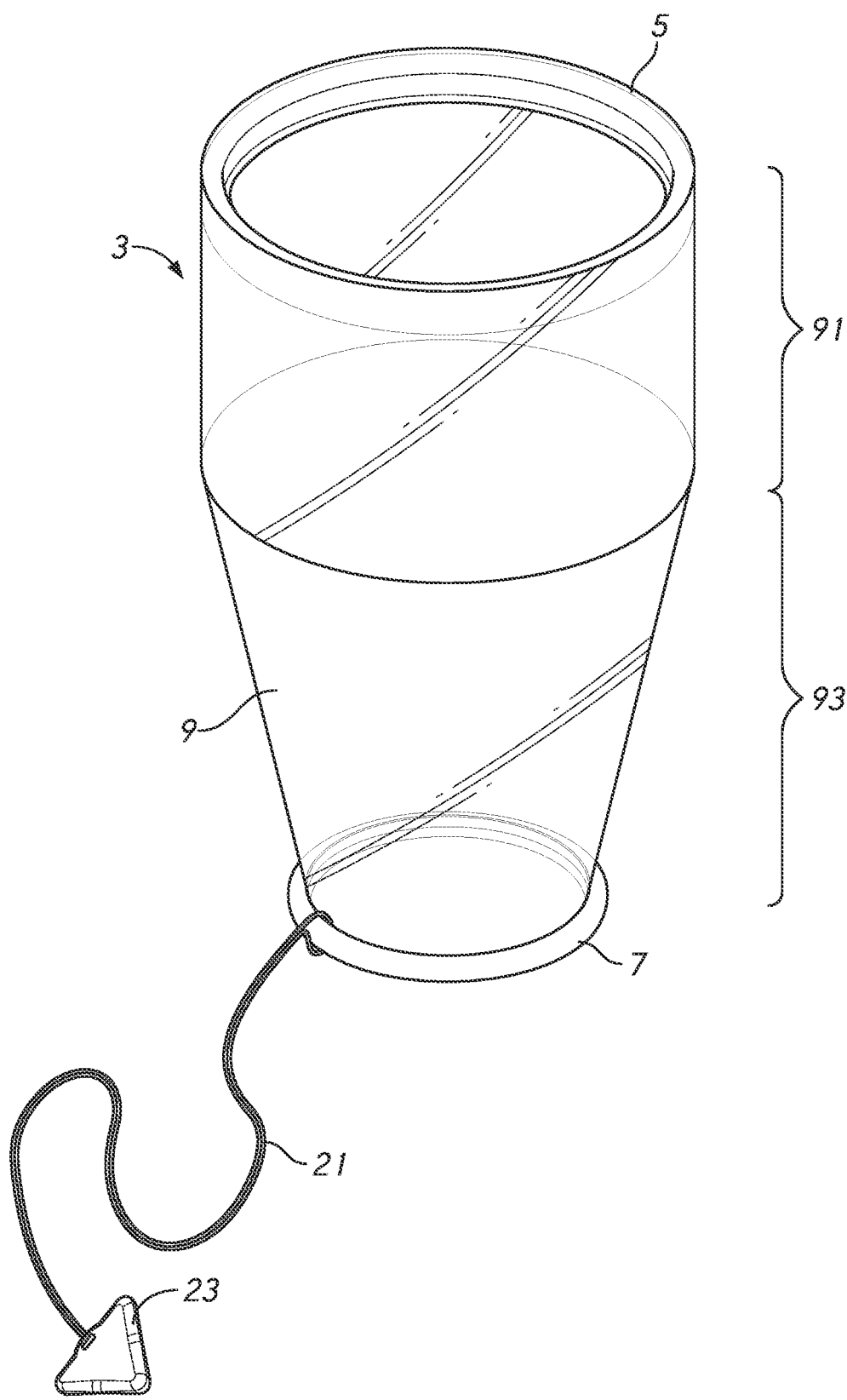
FIGS. 1A-1B are perspective views of a protector/retractor in accordance with various embodiments of the present invention.
Figure 1B:
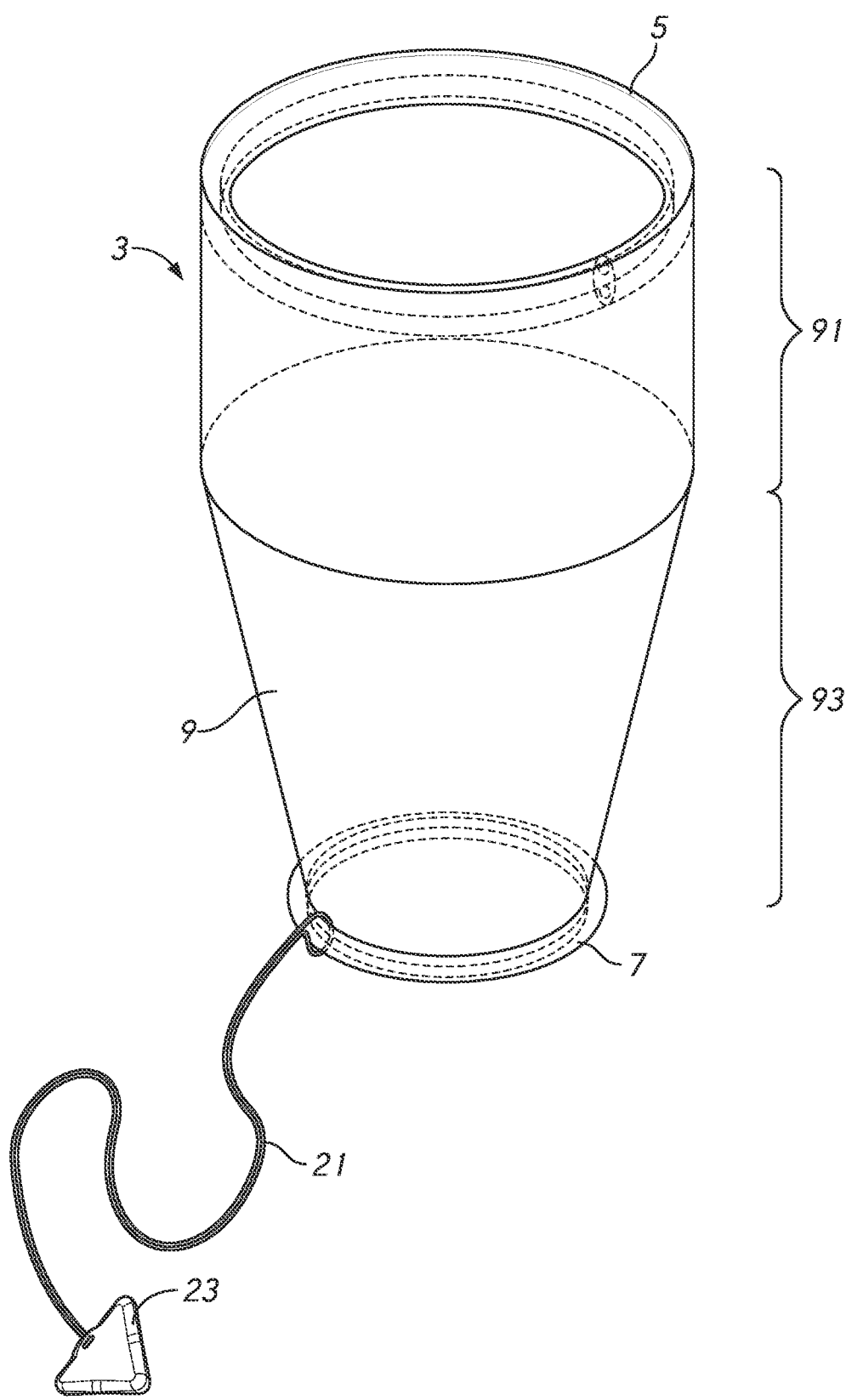
Figure 2A:
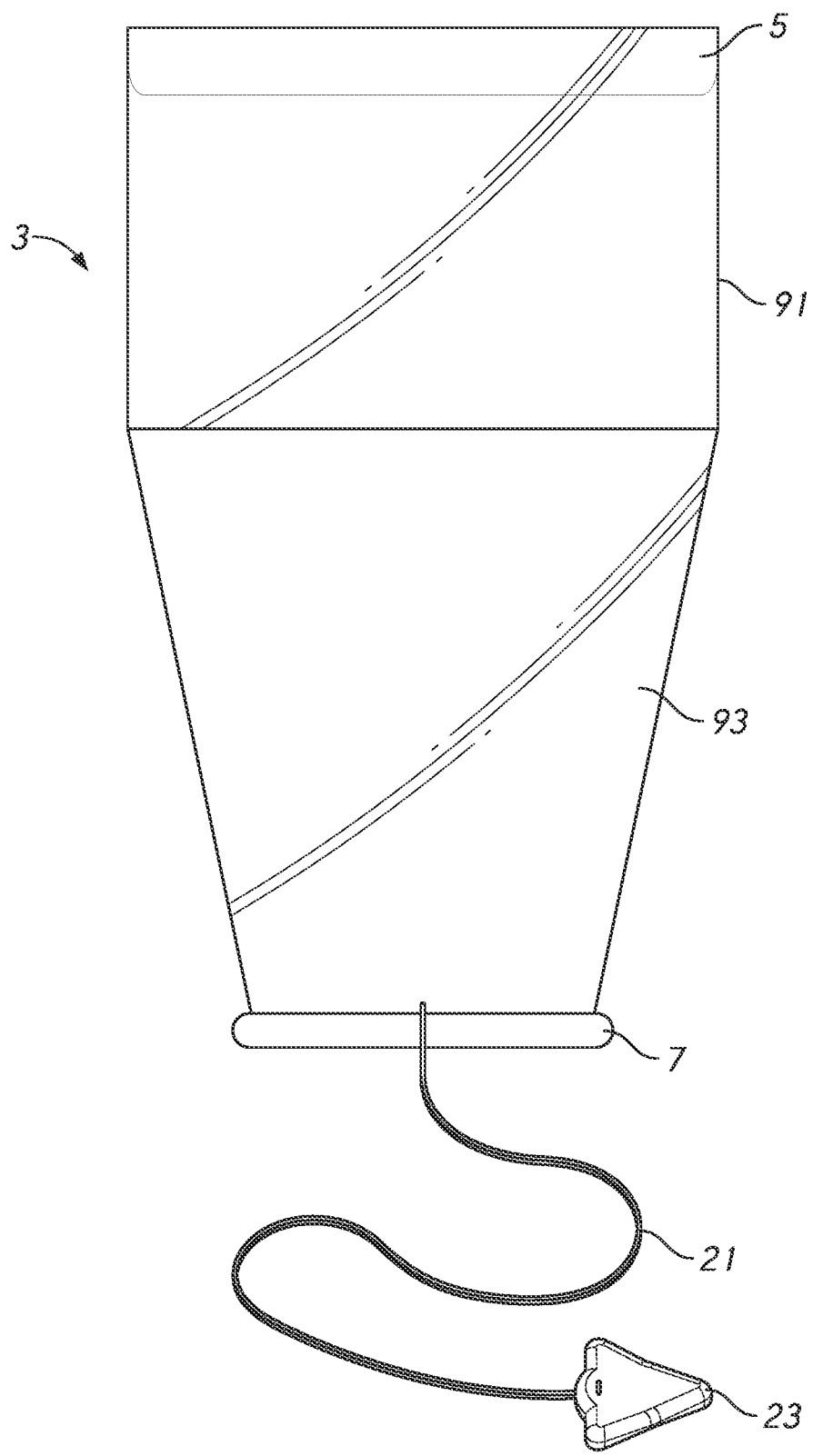
FIGS. 2A-2B are side views of a protector/retractor in accordance with various embodiments of the present invention.
Figure 2B:
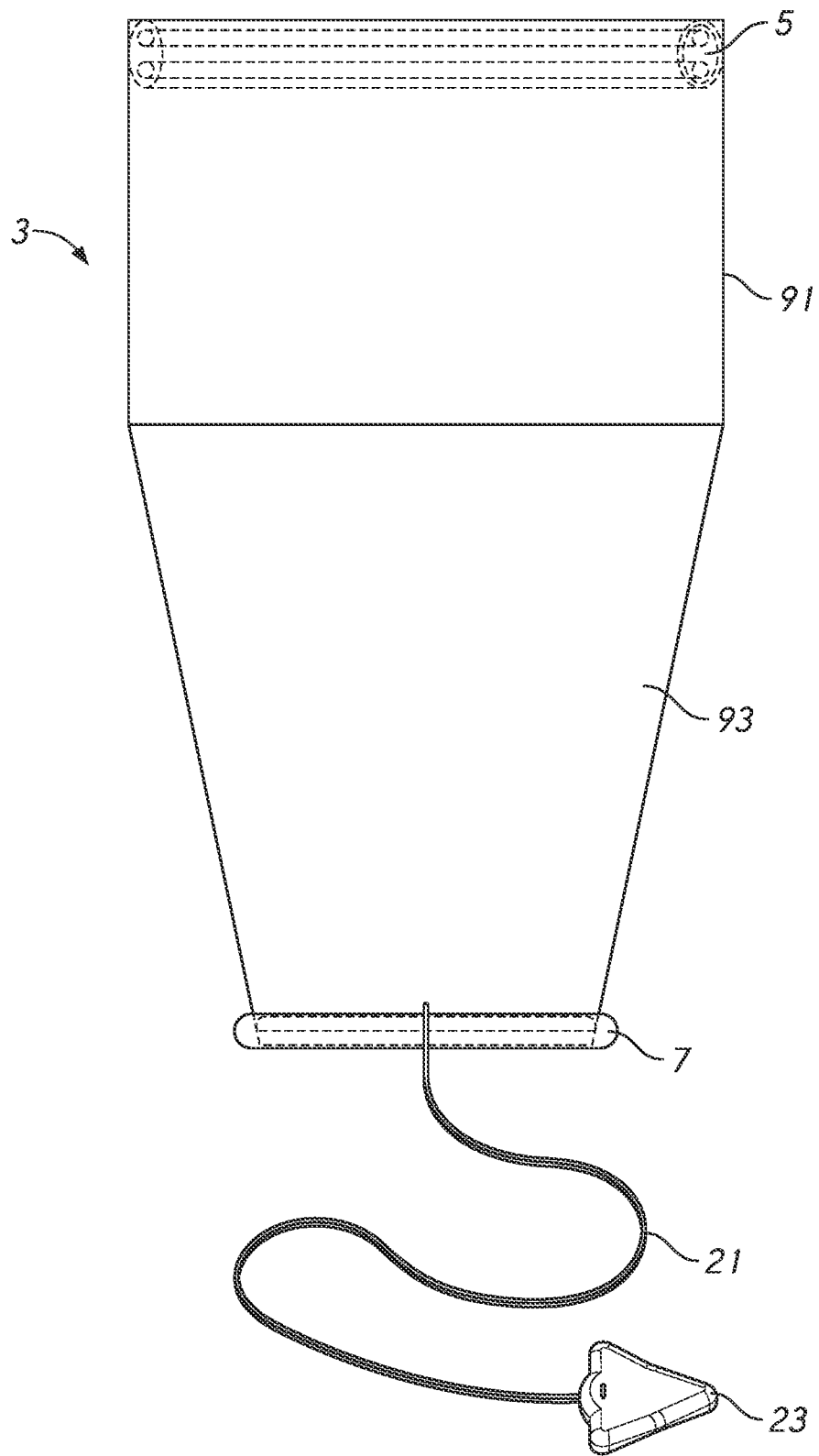
Figure 3A:
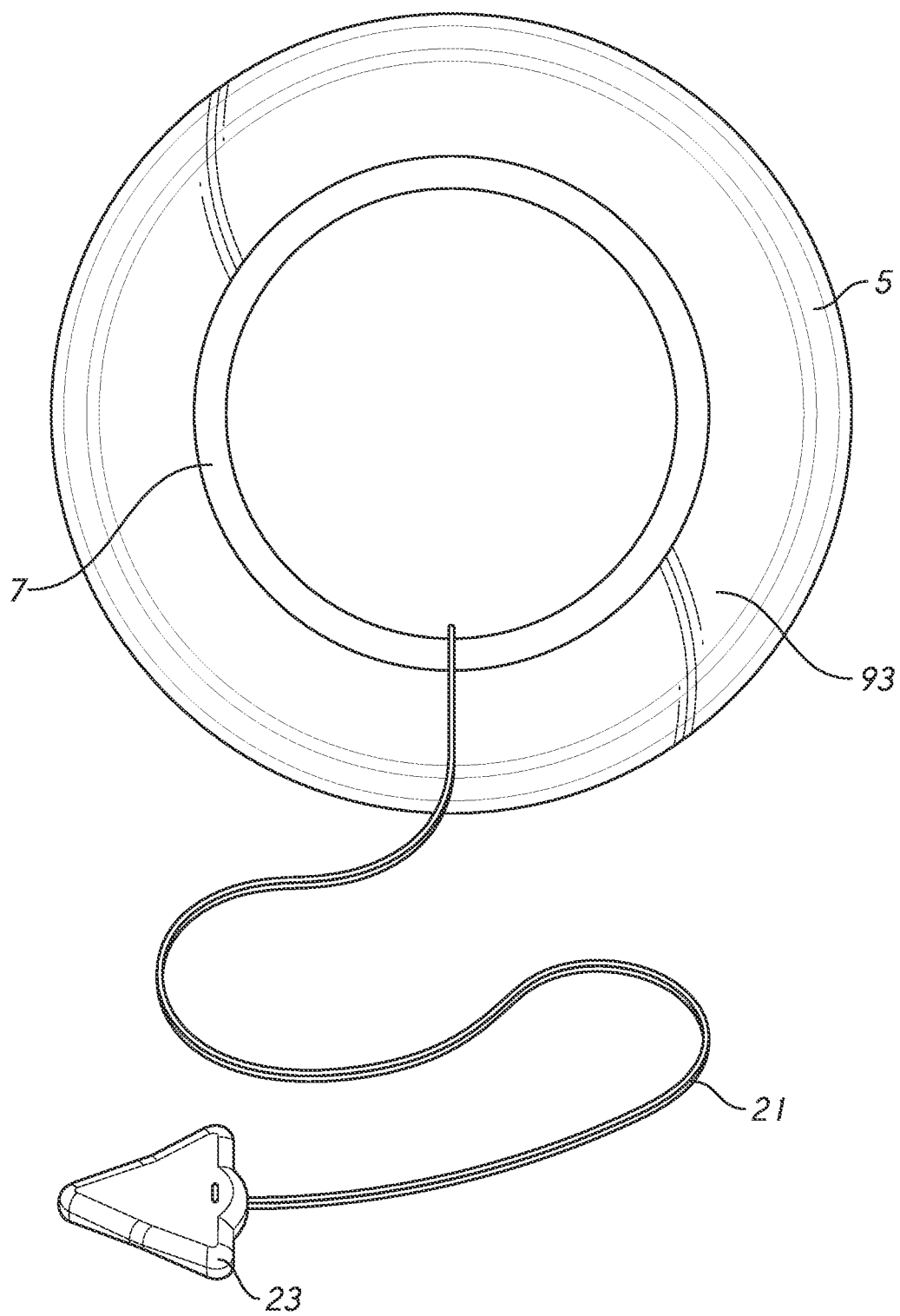
FIGS. 3A-3B are top views of a protector/retractor in accordance with various embodiments of the present invention.
Figure 3B:
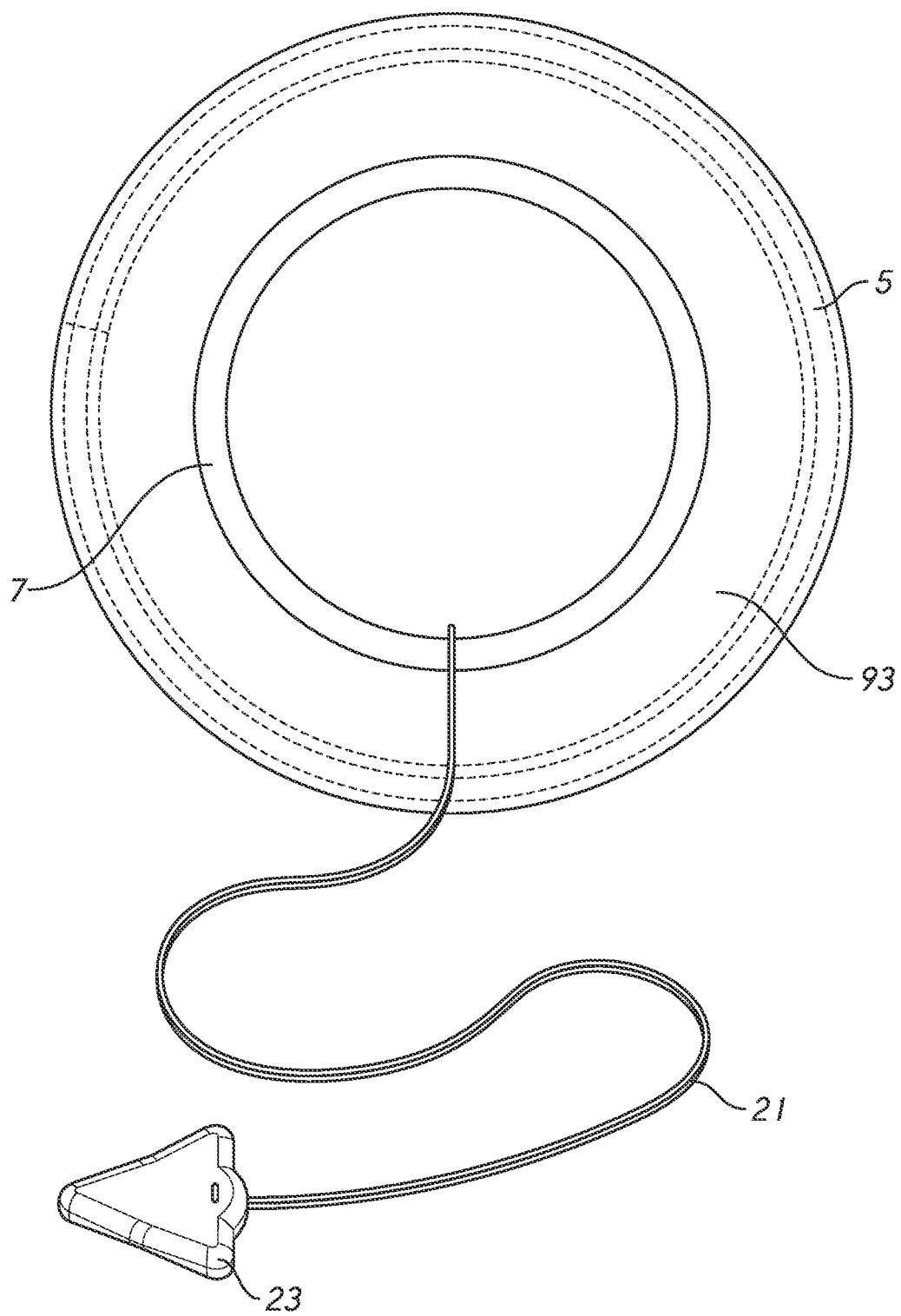
Figure 4A:
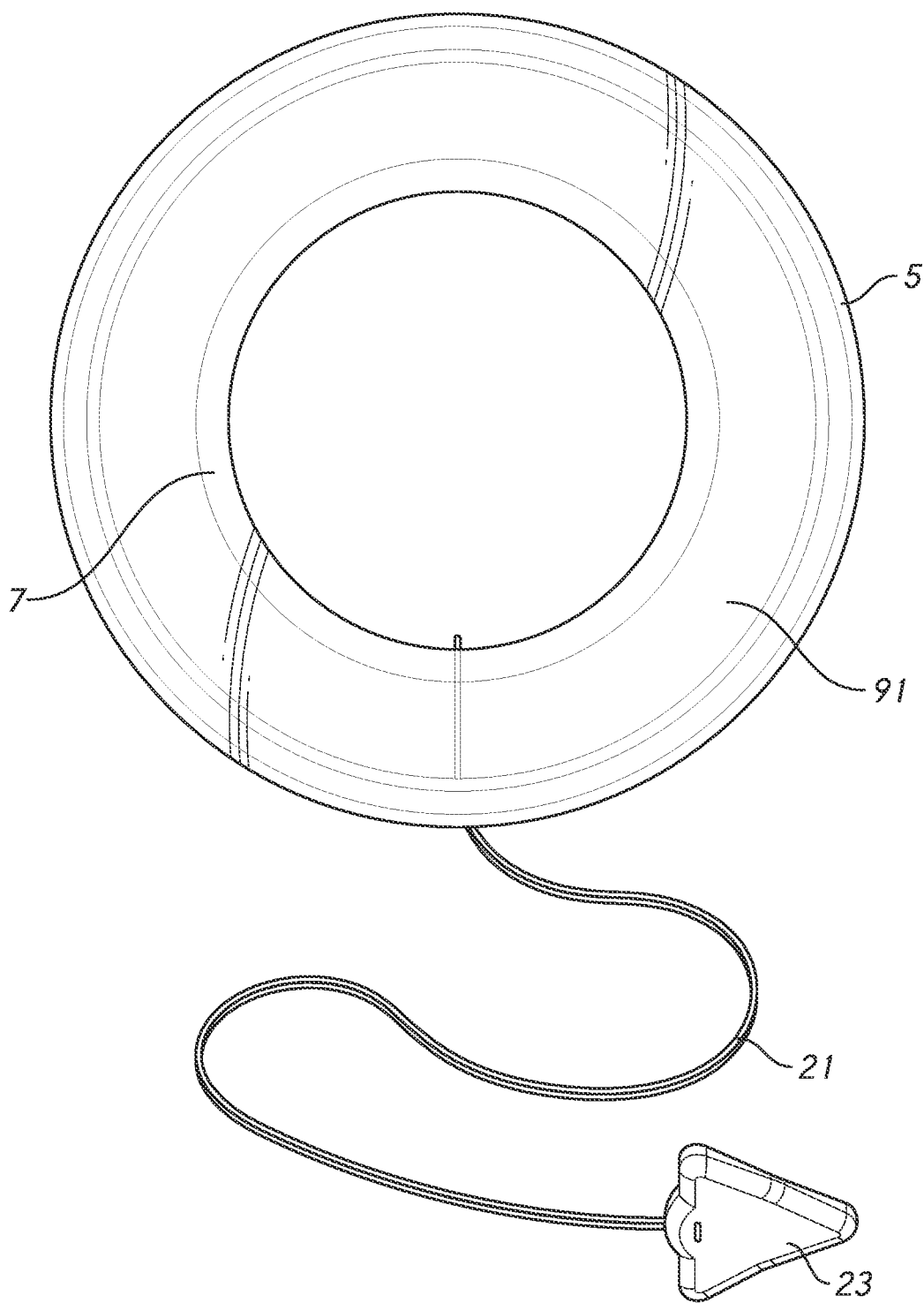
FIGS. 4A-4B are bottom views of a protector/retractor in accordance with various embodiments of the present invention.
Figure 4B:
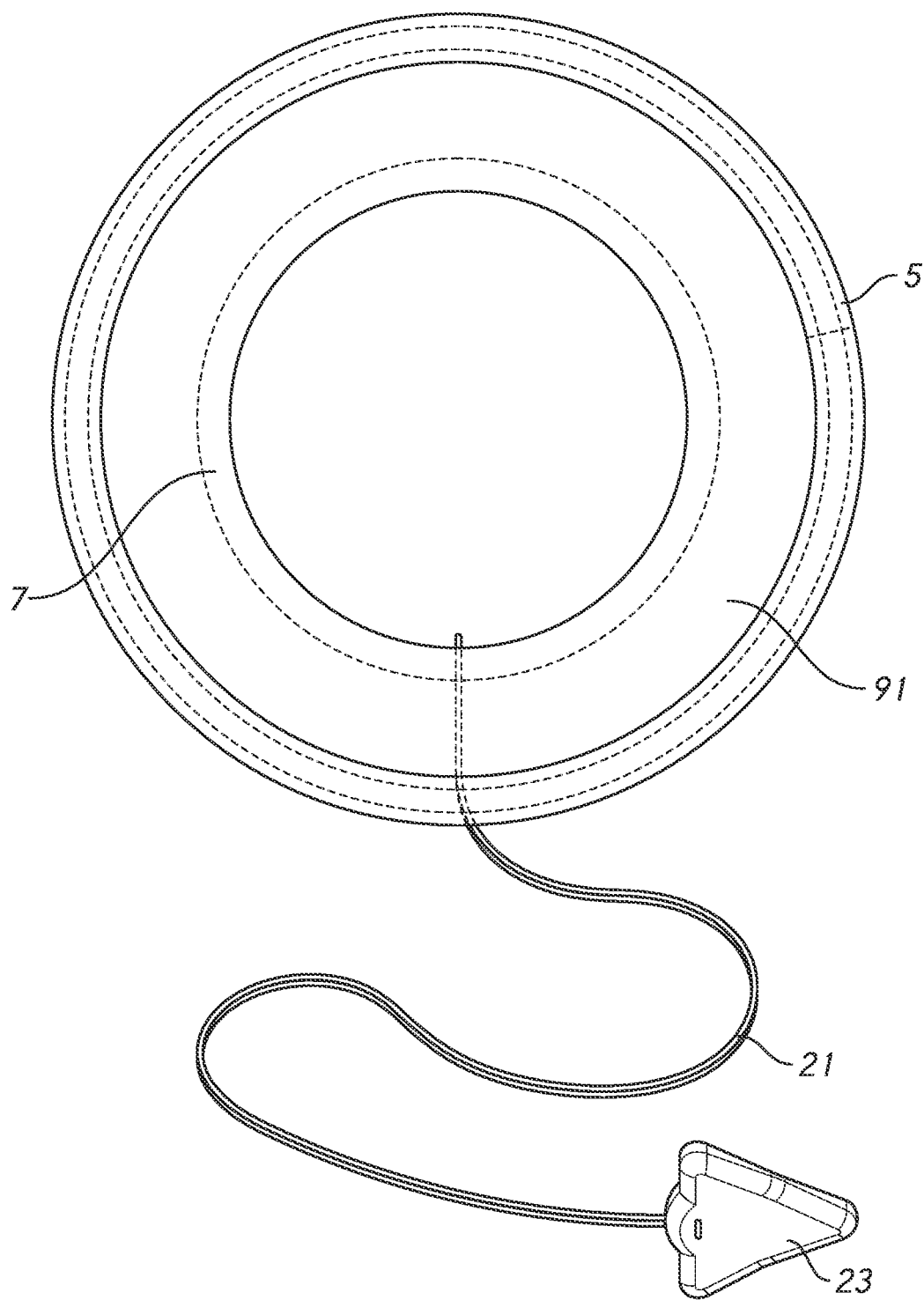
Figure 5:
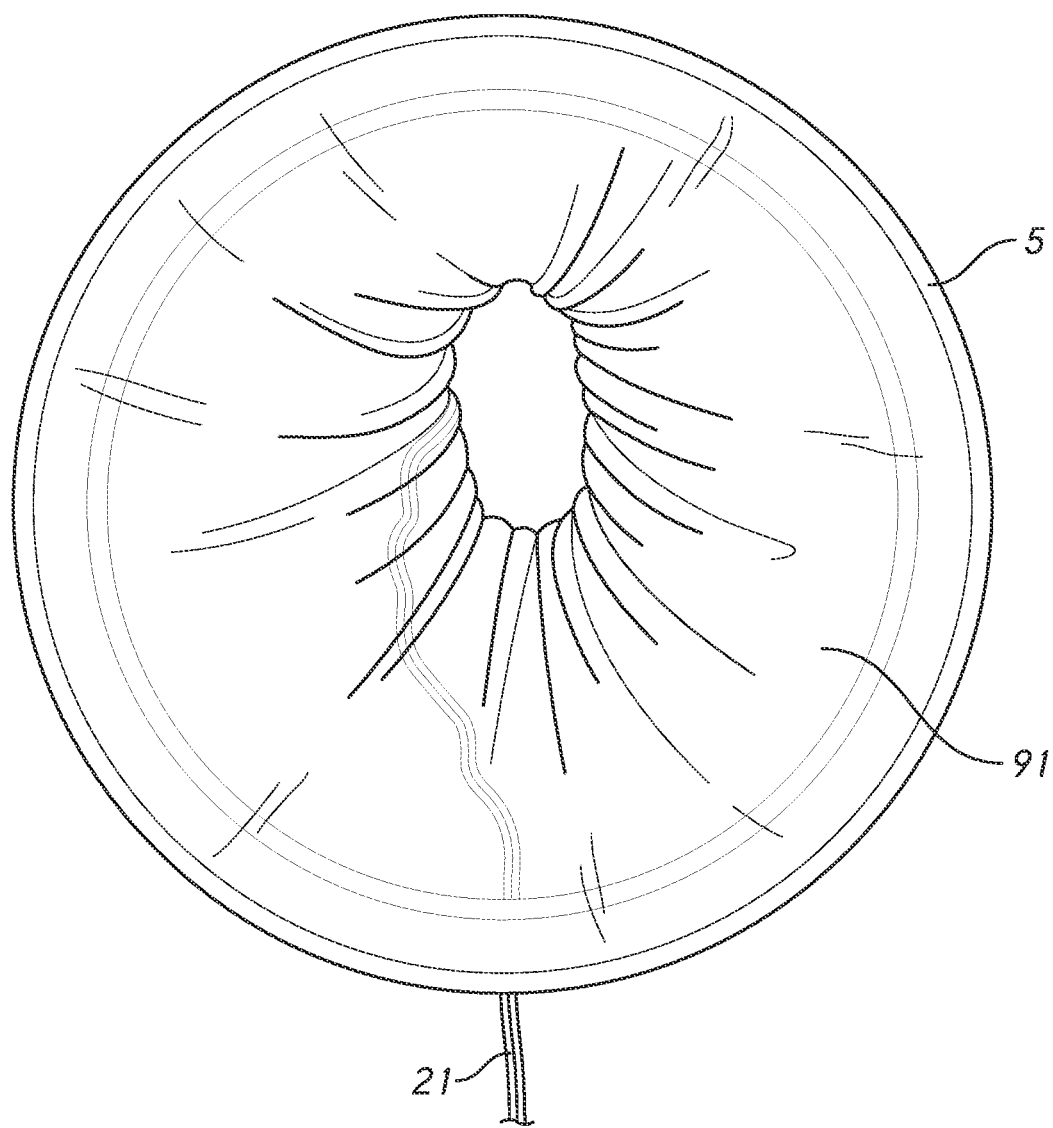
FIG. 5 is a top view of a deployed protector/retractor in accordance with various embodiments of the present invention.
Figure 6:
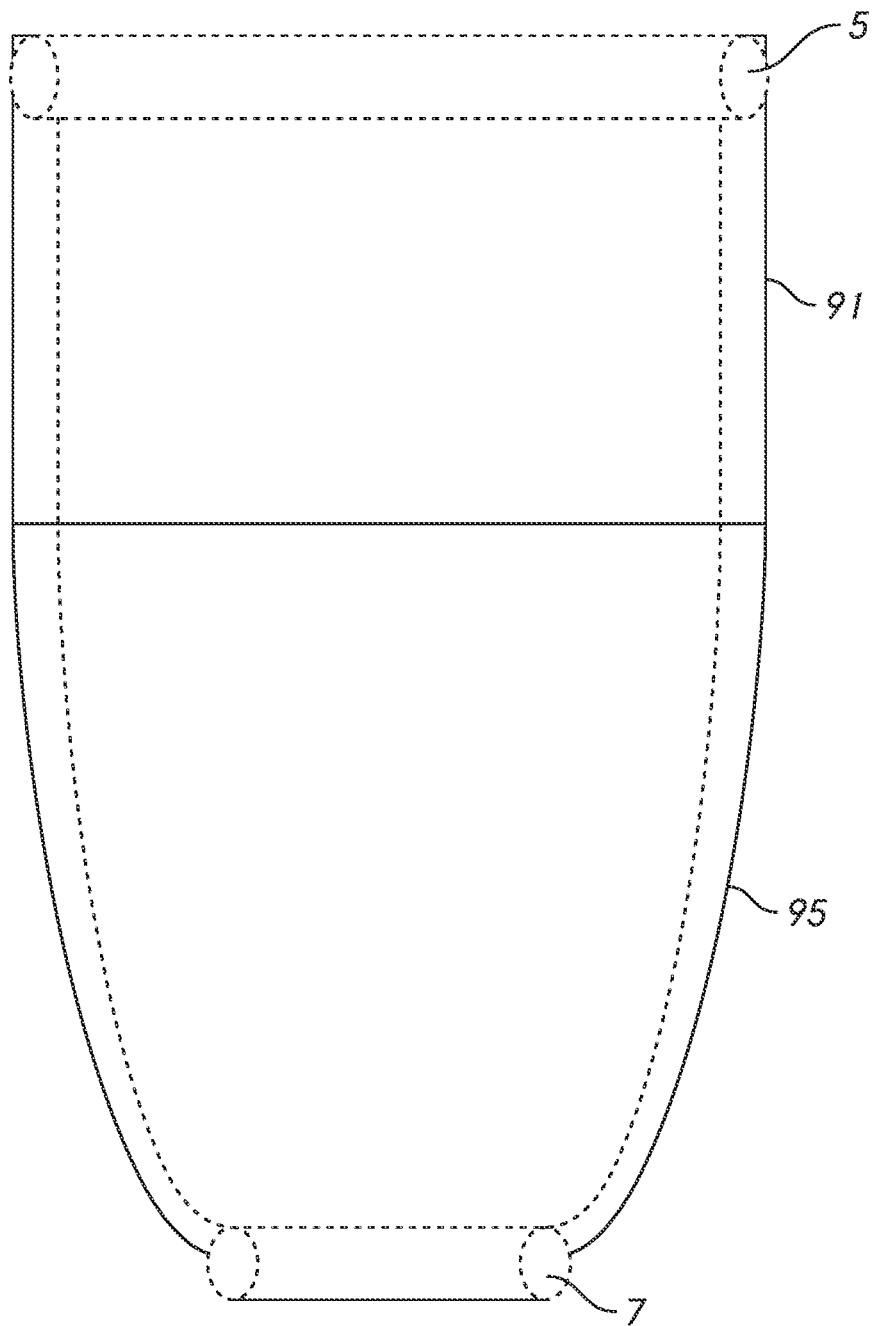
FIG. 6 is a side view of a protector/retractor in accordance with various embodiments of the present invention.
Figure 7:
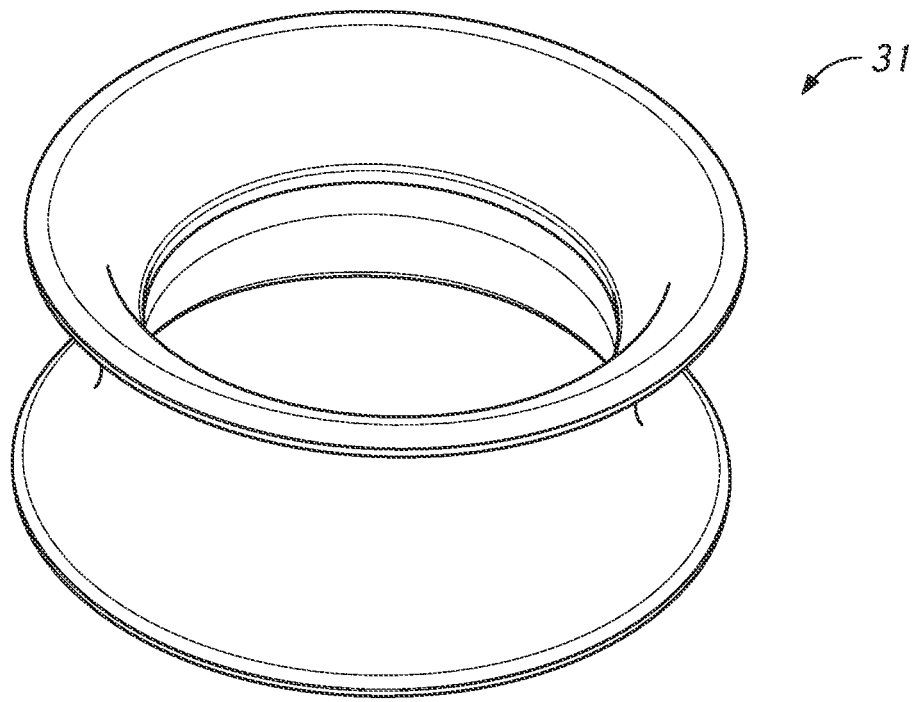
FIG. 7 is a perspective view of a channel or retainer in accordance with various embodiments of the present invention.
Figure 8:
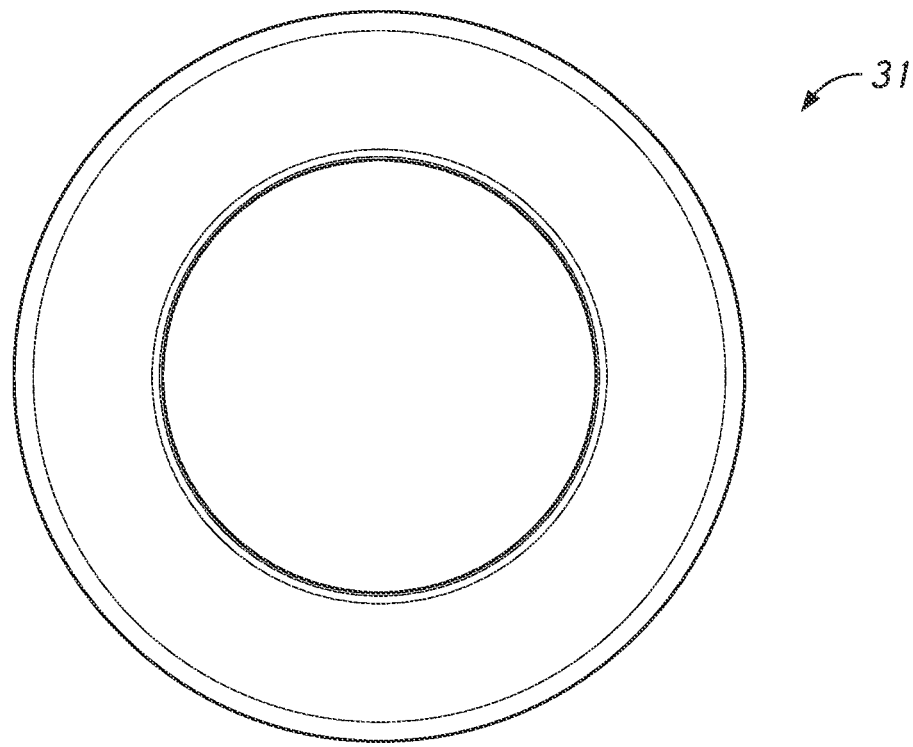
FIG. 8 is a top view of a channel or retainer in accordance with various embodiments of the present invention.
Figure 9:
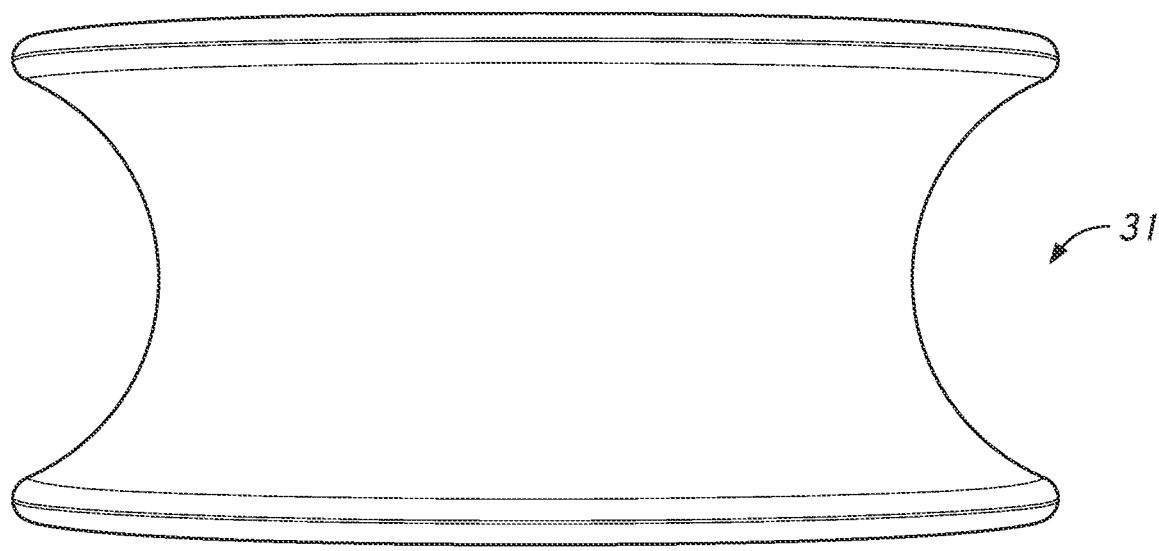
FIG. 9 is a side view of a channel or retainer in accordance with various embodiments of the present invention.
Figure 10:
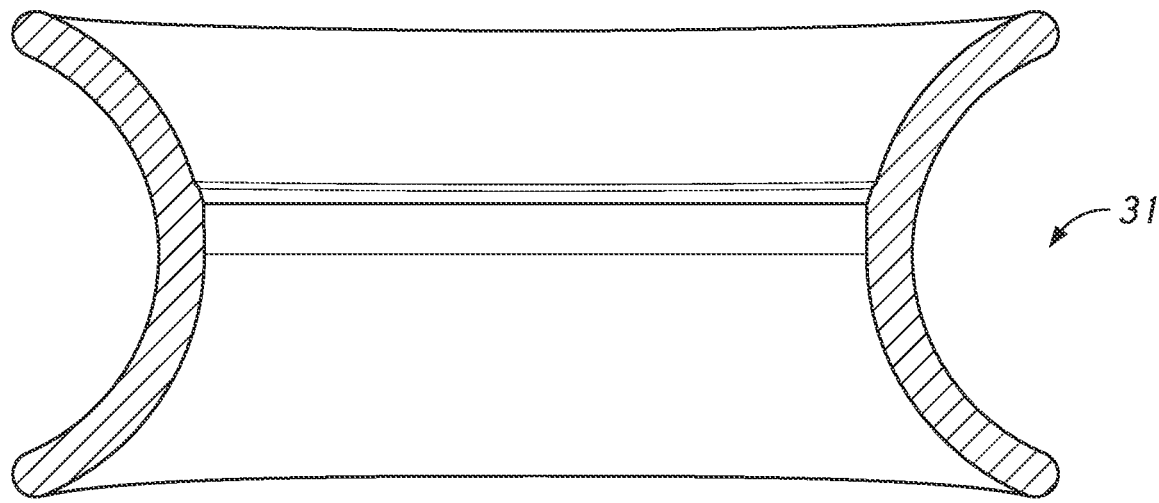
FIG. 10 is a cross-sectional side view of a channel or retainer in accordance with various embodiments of the present invention.
Figure 11A:
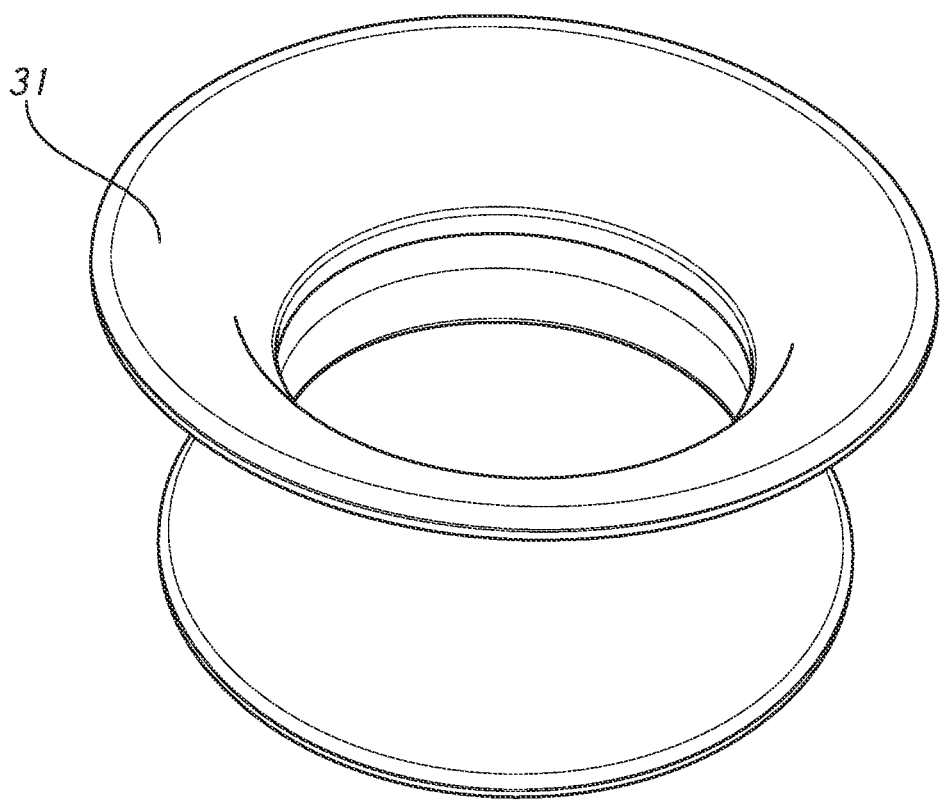
FIGS. 11A-11C are various views of a channel or retainer in accordance with various embodiments of the present invention.
Figure 11B:
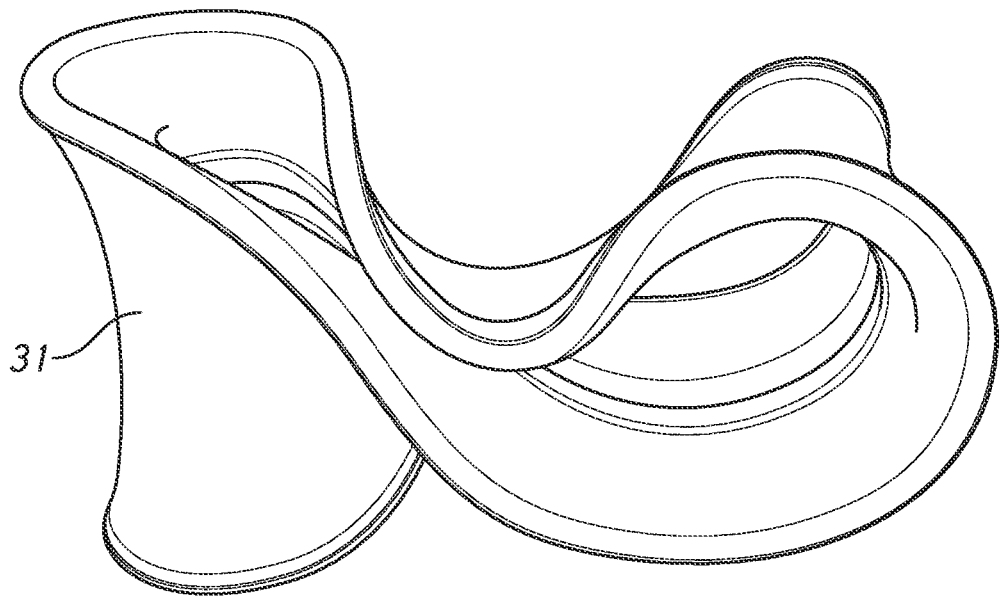
Figure 11C:
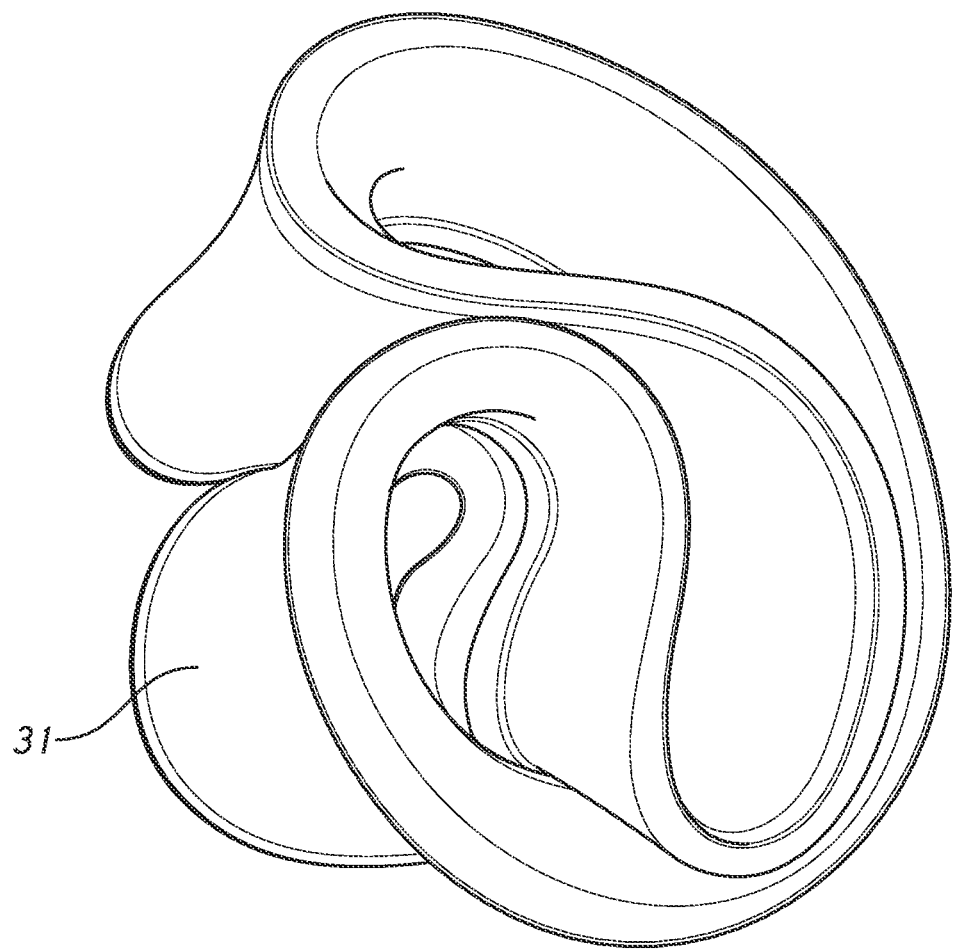
Figure 12:
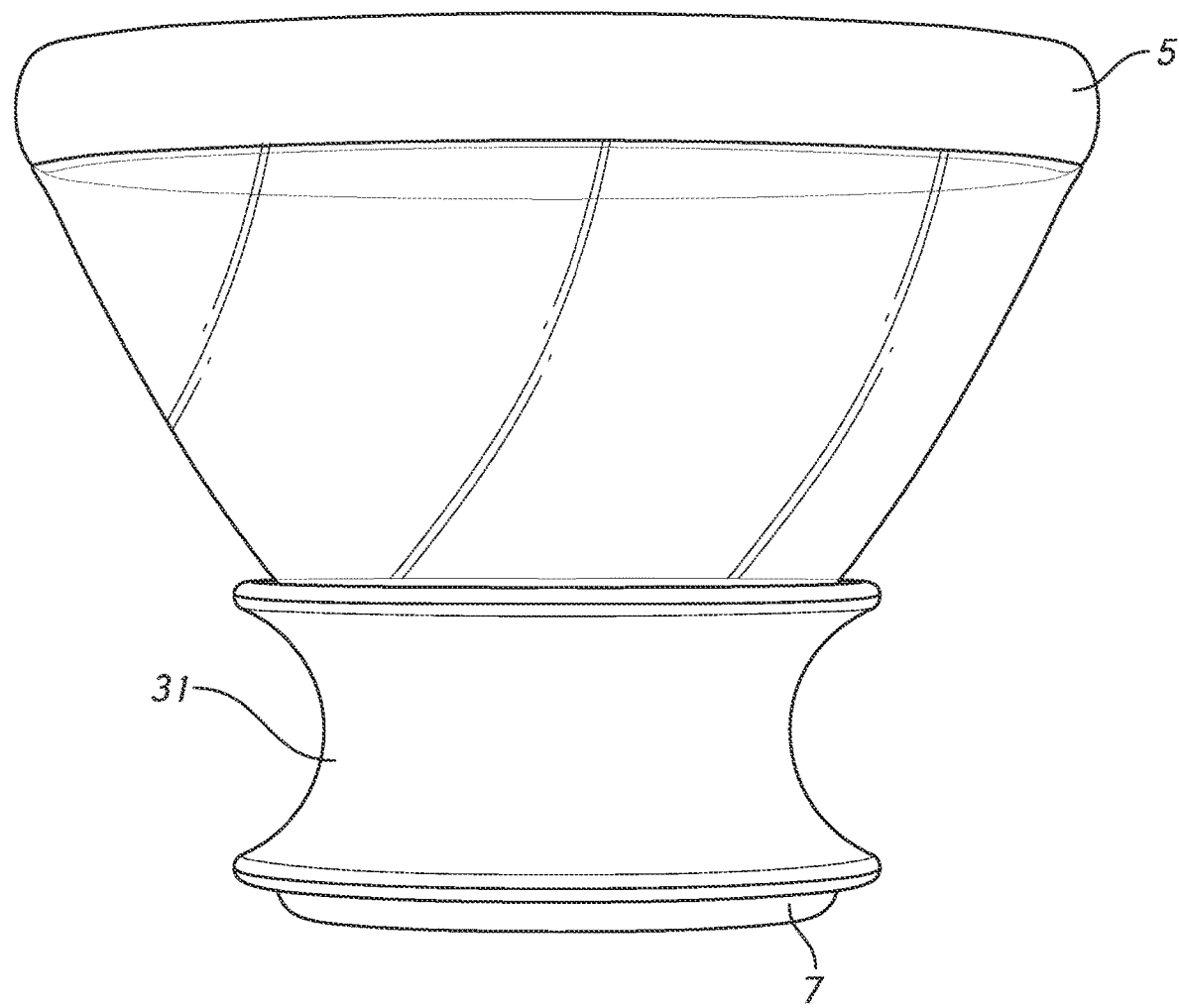
FIG. 12 is a side view of a protector/retractor and a channel or retainer in accordance with various embodiments of the present invention.
Figure 13:
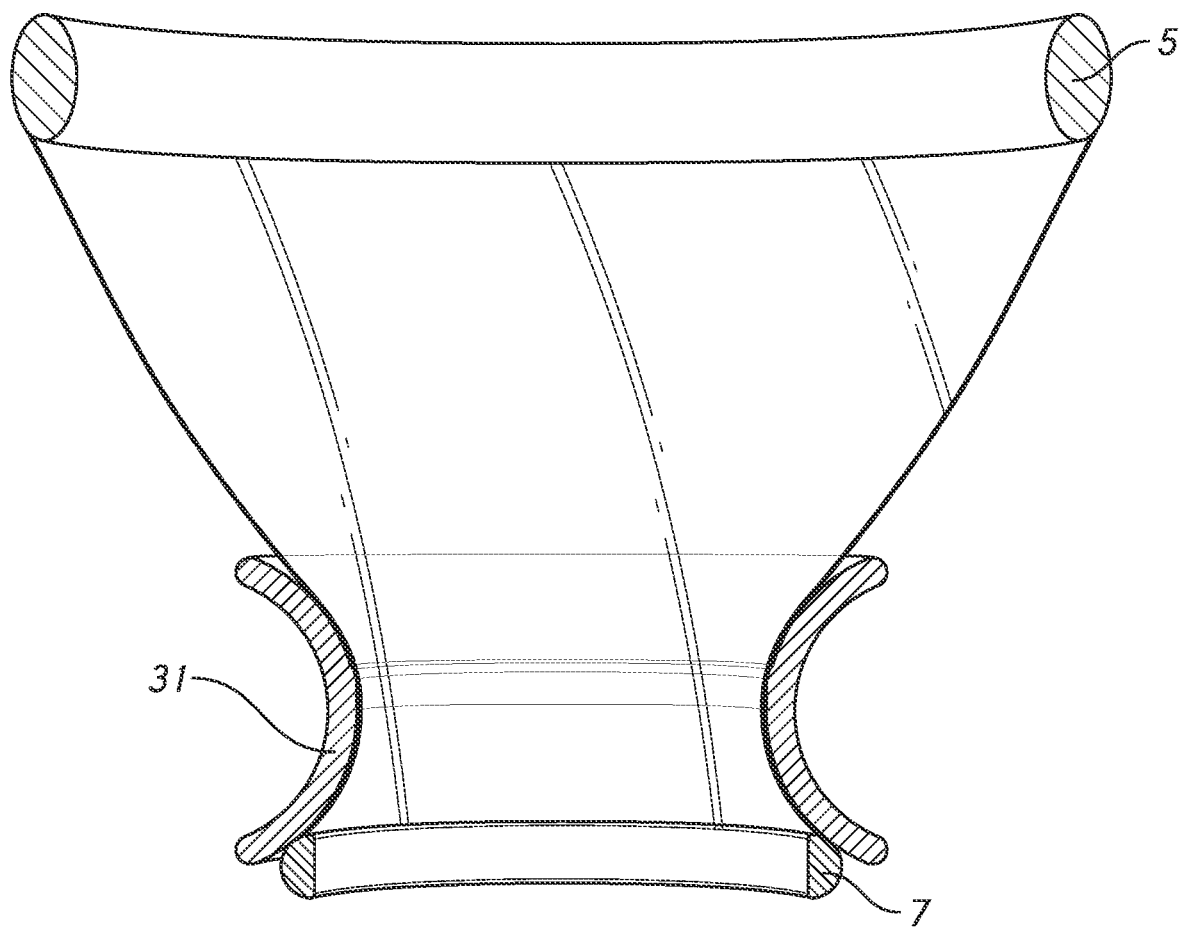
FIG. 13 is a cross-sectional side view of a protector/retractor and a channel or retainer in accordance with various embodiments of the present invention.
Figure 14:
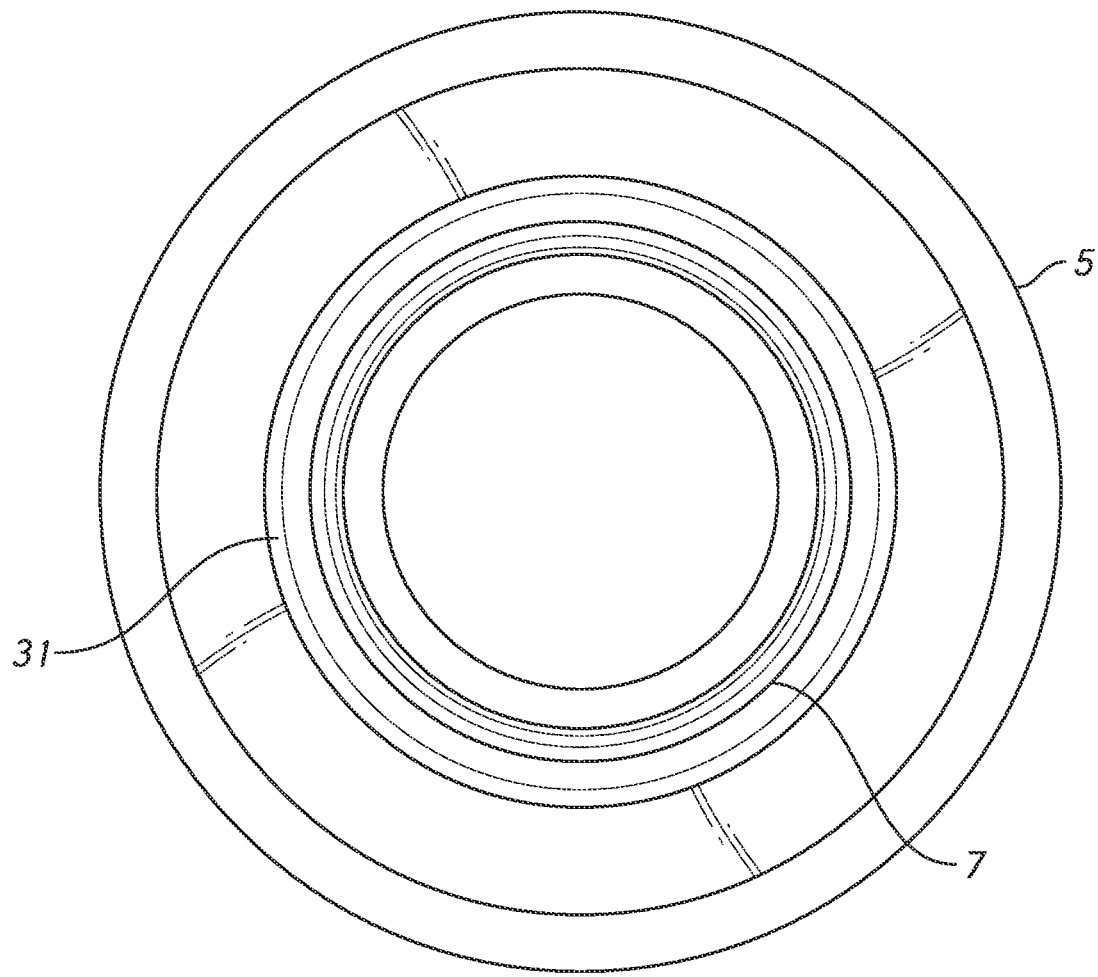
FIG. 14 is a bottom view of a protector/retractor and a channel or retainer in accordance with various embodiments of the present invention.
Figure 15:
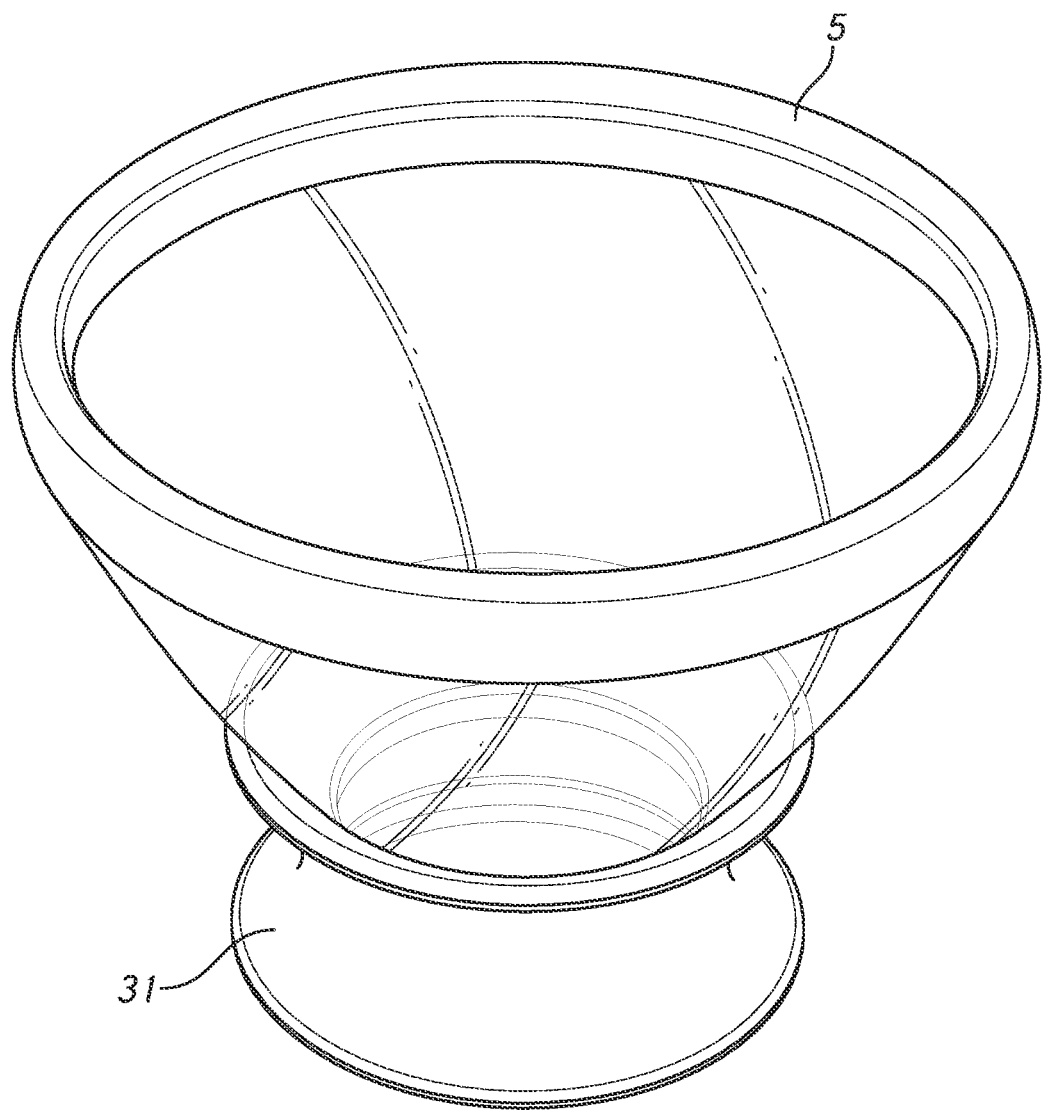
FIGS. 15-16 are perspective views of a protector/retractor and a channel or retainer in accordance with various embodiments of the present invention.
Figure 16:
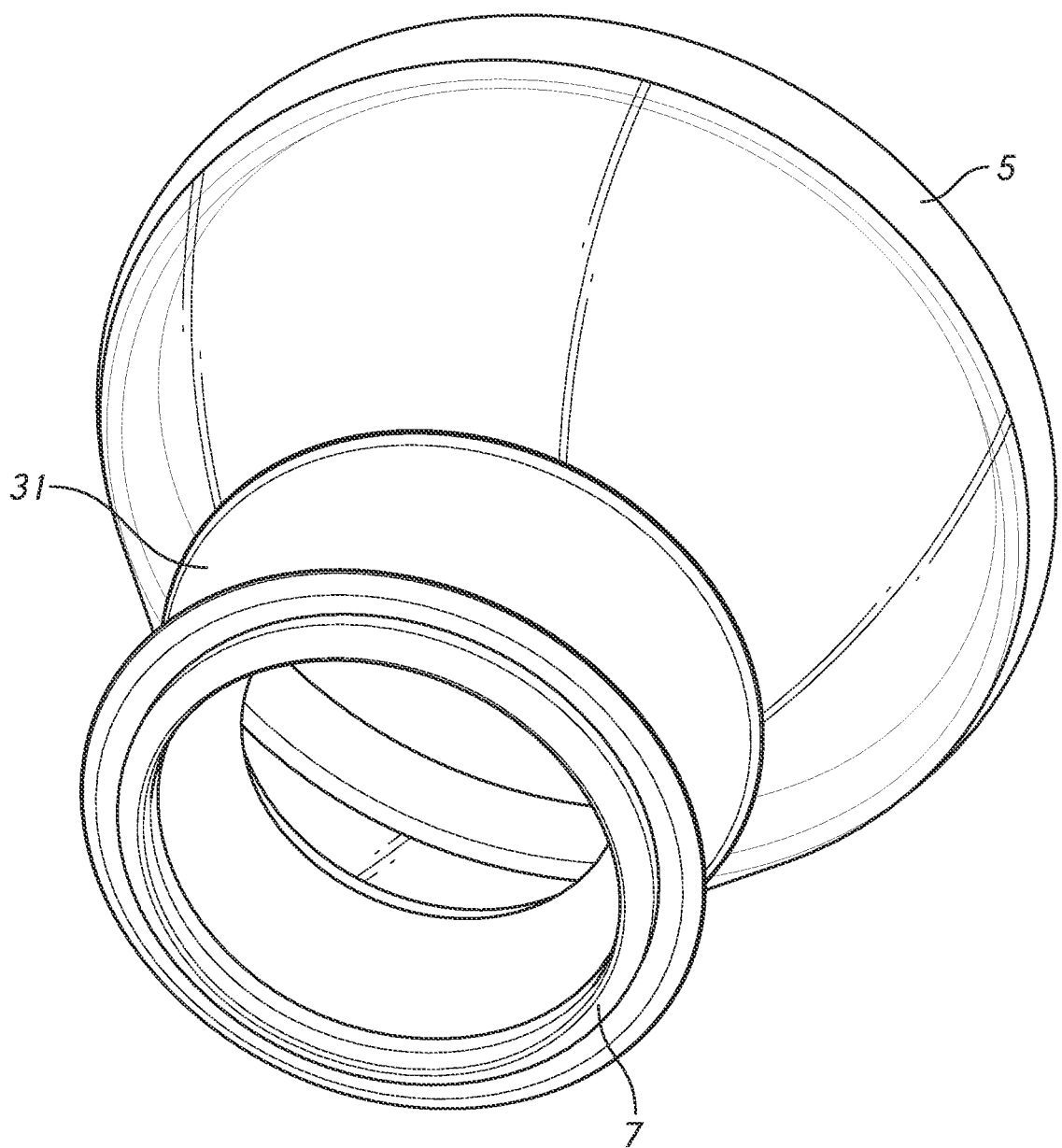
Figure 17:
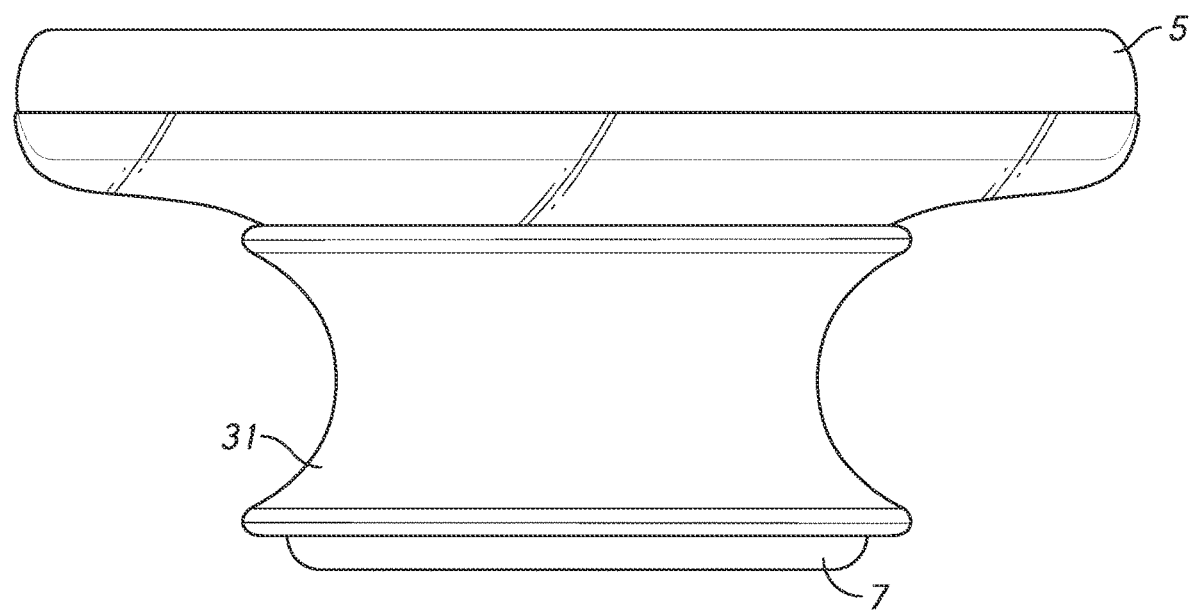
FIG. 17 is a side view of a protector/retractor and a channel or retainer in accordance with various embodiments of the present invention.
Figure 18:
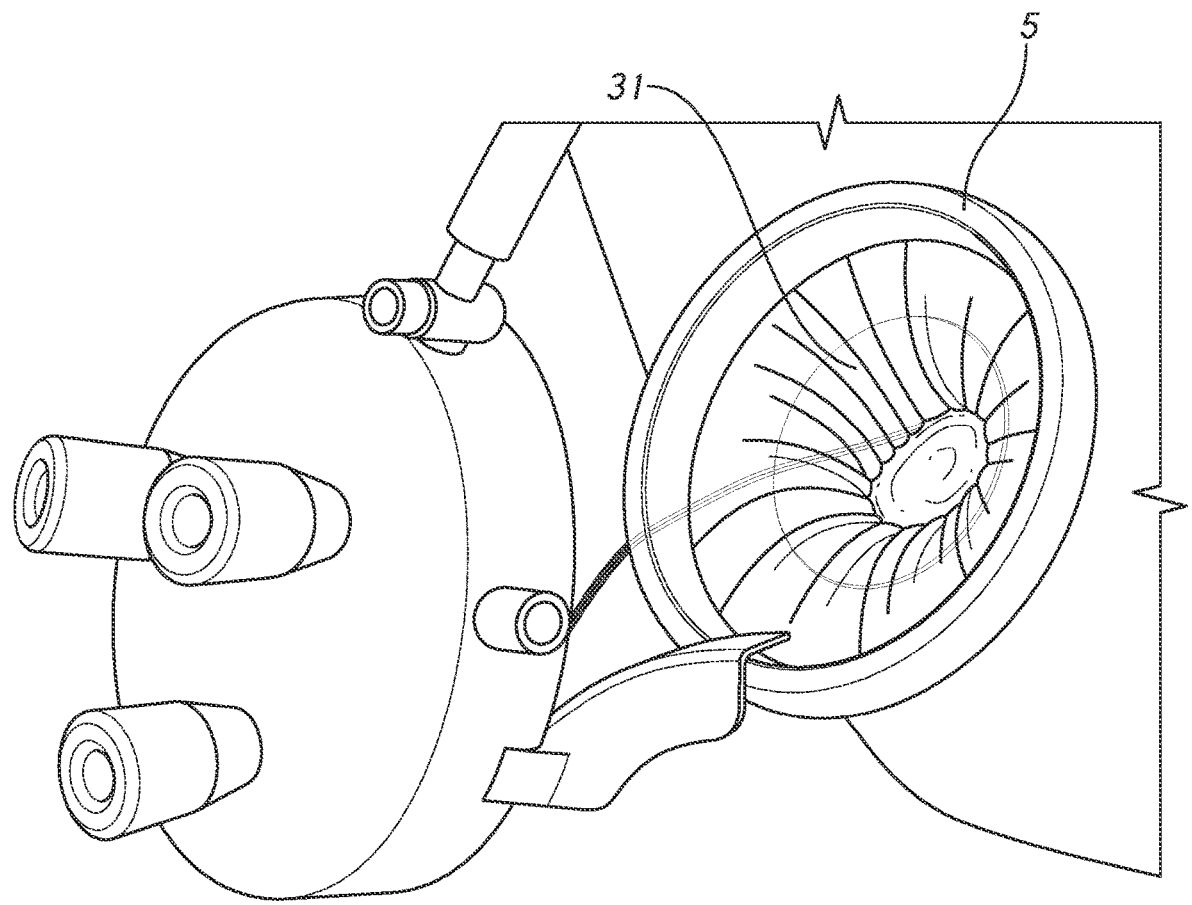
FIG. 18 is a perspective view of a deployed protector/retractor and channel or retainer in accordance with various embodiments of the present invention.

In accordance with various embodiments, protector/retractor apparatuses, systems and/or methods are provided, and various views of various embodiments of exemplary protector/retractor apparatuses, systems and aspects thereof are shown in FIGS. 1-18.

In various embodiments, the retractor system comprises a circumferential protector/retractor (hereinafter referred as "retractor") and/or a self-retaining retainer or channel. In various embodiments, the system provides self-retaining retraction and simultaneous insufflation of the vaginal canal or body cavity, while also allowing for instrument passage and manipulation. The retractor system in accordance with various embodiments allows surgeons to perform various diagnostic and therapeutic procedures within the vaginal canal using endoscopic techniques. One exemplary procedure is an endoscopic colpotomy, which is an incision in the vaginal canal near or around the cervix created while using vaginal insufflation and laparoscopic instrumentation. Through a colpotomy, access into the peritoneal cavity can be gained. The retractor system provides or allows for an endoscopic colpotomy by providing self-retaining retraction, insufflation, and scope/instrument access. In various embodiments, the system may be used for other procedures that require endoscopic access and/or endoscopic access with insufflation of the vaginal canal or body cavity. In various embodiments, a sealing cap may be attached to the retractor and trocar sleeves and/or instrumentations may be inserted therethrough. In various embodiments, an insufflation stabilization bag system may be connected to the retractor system to mitigate pulsing/billowing in the vaginal canal or body cavity. In accordance with various embodiments, the retractor system provides the establishment of insufflation of the vaginal canal (pneumovagina) or body cavity, allowing for the passage of instruments for various diagnostic and therapeutic procedures (e.g. colpotomy creation using endoscopic techniques).

In accordance with various embodiments, a retractor 3 is provided for the deployment into a patient's cavity, e.g., the abdominal cavity for open or laparoscopic surgeries or the peritoneal cavity during transvaginal natural orifice transluminal endoscopic surgery (vNOTES). The retractor, in accordance with various embodiments, comprises an external or upper portion comprising an external support or outer ring connected to a sheath having an upper portion or segment. The upper segment 91 of the sheath in accordance with various embodiments has a shape that matches the outer profile or footprint of the external support. In various embodiments, the upper segment 91 has a circular or cylindrical shape. In accordance with various embodiments, the external or upper portion of the retractor facilitates external atraumatic placement and manipulation of the retractor and attachment of additional surgical devices, such as sealing caps, lighting and/or insufflation units, and the like. The external or upper portion also provides increased retraction and triangulation. In accordance with various embodiments, the retractor comprises an internal or lower portion comprising an internal support or ring connected to a sheath having a lower portion or segment. The lower segment 93 of the sheath in accordance with various embodiments has a shape that on one end matches the outer profile or footprint of the external support or outer ring and on an opposing end matches the inner profile or footprint of the internal support or inner ring. In various embodiments, the lower segment has a conical, truncated conical or frustoconical shape. In accordance with various embodiments, the internal or lower portion or segment facilitates atraumatic placement and anchoring of the retractor within a patient's cavity.

The retractor 3, in various embodiments, provides circumferential or 360 degrees of protection and/or retraction of an opening or orifice of a patient, providing unobstructed access into a patient's body or cavity. The retractor comprises an outer ring or support 5 and an inner ring or support 7. The upper or outer ring 5 is arranged to be placed or secured outside of the patient for ease of accessibility, adjustment of the retraction force and/or placement of the retractor. In various embodiments, an instrument port, sealing or gel cap may be attached to the outer or external ring 5 of the retractor. The lower or inner ring 7 is insertable through a patient's opening, such as an incision or natural orifice, anchoring of the retractor within the patient. The inner ring 7 is smaller than the outer ring 5. In various embodiments, the outer ring 5 has a diameter greater than the inner ring 7.

The inner and outer rings are connected by a film, fabric, membrane, or sheath 9. In various embodiments, the retractor is adjustable in length, e.g., shortening the distance between the rings, by, for example, rolling the sheath 9 around the outer ring 5, and such adjustment can apply a retraction or radial force to retract or enlarge an opening in a patient. The retractor, in various embodiments, is adjustable in length or otherwise adjustable to accommodate different patient body types or body wall thickness.

The retractor is sufficiently flexible to be atraumatic when the retractor is deployed or otherwise placed through and disposed in the opening of the patient. In various embodiments, the sheath 9 is made of an elastomeric or non-metallic material to be atraumatic and/or not or minimally thermally conductive when the retractor is in operation or deployed or otherwise placed through and disposed in the opening of the patient. In various embodiments, the sheath 9 is made of one or more layers of material and in various embodiments is anisotropic, e.g., stretchable or extendable longitudinally but not or minimally radially, being made of or including one or more layers of a fabric or similar materials with such anisotropic characteristics.

In accordance with various embodiments, the sheath 9 comprises an upper segment 91 and a lower segment 93. The upper segment 91 has a proximal end attached to the outer ring 5 and a distal end attached and/or extending to the lower segment 93. The upper segment 91, in various embodiments, has a circular or cylindrical shape. The lower segment 93 has a distal end attached to the inner ring 7 and proximal end attached to and/or extending from the upper segment 91. The lower segment 93 of the sheath 9, in accordance with various embodiments, has a truncated conical shape which tapers from the distal or bottom end of the upper segment 91 to the inner ring 7. In various embodiments, the upper segment 91 has an outer diameter that matches or closely matches an outer diameter of the outer ring 5. The upper segment 91 has a constant outer diameter extending from its proximal end to its distal end. The constant diameter of the upper segment 91 of the sheath 9 allows the outer ring 5 to be flipped, rotated or rolled, gathering up or shortening proximal portions of the upper segment 91, as the upper segment is rolled, wrapped or wound around an outer surface of the outer ring 5, a predefined or predetermined number of times with reduced or without increased film or material tension of the sheath 9 around the outer ring 5 and with minimal effort, as the difficulty of flipping or rolling the outer ring 5 is driven in large part by an increase in film tension with each additional flip. This difficulty can be increased with outer rings that are rigid, e.g., outer rings with an internal or external rigid hoop or segment, although such outer rings can be useful as being sufficiently rigid to connect and seal to a sealing cap or laparoscopic port. This may also lead to difficulty for the user due to the increased force that must be applied to achieve higher amounts of retraction. Furthermore, applying excess force to flip the outer ring could compromise film integrity near the outer ring due to the increased film tension with each additional flip. Additionally, over-tensioned film near the outer ring can also cause the film to be pulled inward, narrowing the access channel or path of instrument entry and potentially increasing susceptibility to potential damage caused by sharp instrumentation. As such, the retractor, in accordance with various embodiments, achieves a higher amount of retraction compared to a non-uniform or non-constant diameter sheath or upper segment of a sheath, such as a fully conical sheath, while also not compromising film or material integrity of the sheath. In accordance with various embodiments, the cylindrical or constant diameter upper segment helps reduce film tension by maintaining a sheath diameter that matches the outer ring diameter with each additional flip.

In various embodiments, the lower segment 93 has an outer diameter at its distal end that matches or closely matches an outer diameter of the inner ring 7. In various embodiments, the lower segment 93 has an outer diameter at its proximal end that matches or closely matches an outer diameter of the outer ring 5 and/or an outer diameter of the upper segment 91. The lower segment 93 is curved, angled, or tapered having a larger upper diameter relative to a smaller lower diameter. In various embodiments, the lower segment 93 has a constant angle or straight taper extending from its proximal end to its distal end. In various embodiments, the lower segment, e.g., lower segment 95, has a curved or arcuate taper extending from its proximal end to its distal end. The tapered, lower sheath segment still allows for the sheath 9 to be attached to the smaller diameter inner ring, relative to a larger diameter outer ring or upper segment, for use in similarly small or dimension incisions, opening, orifices and/or anatomical entries, channels or spaces. In accordance with various embodiments, the angle of the tapered lower segment or progressively decreasing diameter lower segment 93 is constant as well as symmetrical to ensure constant tension around the entire circumference of the sheath 9. As such, this maximizes retraction and maintains or maximizes an air-tight seal against a patient body or body wall and/or a sealing cap or laparoscopic port, while the body cavity or anatomical space is insufflated.

The smaller inner ring allows or facilitates insertion of the inner ring and/or portions of the lower segment 93 of the sheath 9 through similarly small or dimensioned incisions, opening, orifices and/or anatomical entries, channels, or spaces. In various embodiments, the outer ring 5, the upper segment 91 of the sheath 9, and/or the proximal end of the lower segment 93 of the sheath 9 has a diameter between about 4 to 5 inches (10.16 cm to 12.7 cm) and in various embodiments, the outer ring 5, the upper segment 91 of the sheath 9, and/or the proximal end of the lower segment 93 of the sheath 9 has a diameter of about 4.4 inches (11.176 cm). In various embodiments, the outer ring diameter matches the upper segment diameter to ensure or allow for the upper segment 91 of the sheath 9 to be welded to the outer ring 5. In accordance with various embodiments, the outer ring 5, the upper segment 91 of the sheath 9, the proximal end of the lower segment 93 of the sheath 9 or any combinations thereof have approximately the same diameter. In various embodiments, the inner ring 7 and/or a distal end of the lower segment 93 of the sheath 9 has a diameter between about 2 to 3 inches (5.08 cm to 7.62 cm) and in various embodiments, the inner ring 7 and/or distal end of the lower segment 93 of the sheath 9 has a diameter of about 2.8 inches (7.112 cm). In various embodiments, the outer ring 5, the upper segment 91 of the sheath 9, and/or the proximal end of the lower segment 93 of the sheath 9 has a diameter larger than the inner ring diameter and/or the diameter of the distal end of the lower segment 93 of the sheath 9 and in various embodiments about 1 to 2 inches (2.54 cm to 5.08 cm) larger. In various embodiments, a larger outer ring diameter relative to the inner ring diameter enhances retraction and/or provides a larger platform for a sealing cap or laparoscopic port and thus unobstructed or enhanced triangulation of instruments. In accordance with various embodiments, the inner ring diameter and/or the diameter of the distal end of the lower segment 93 of the sheath 9 is predetermined or limited by the predetermined or limited size of the incision, the internal anatomy and/or the surgical application. In various embodiments, the inner ring 7 and/or the diameter of the distal end of the lower segment 93 of the sheath 9 is sized and arranged to fit through a linear colpotomy. In accordance with various embodiments, the inner ring diameter and the diameter of the distal end of the lower segment 93 of the sheath 9 are approximately the same. In various embodiments, the inner ring 7 is more flexible or less rigid than the outer ring 5. In various embodiments, the inner ring 7 has one or more detents, apertures, slits, or the like to facilitate collapsing or folding of the inner ring 7 to facilitate insertion and/or anchoring of the inner ring 7. In various embodiments, the inner ring 7 is deformable, compressible, or collapsible, e.g., deforms from a generally circular shape to generally oblong or folded shape, e.g., inner portions of the inner ring 7 are moved near or touching opposing inner portions of the inner ring 7, and/or biased or resilient to return or resume its original or initial undeformed or compressed shape. In various embodiments, a tether 21 and tether tag 23 are attached to the inner ring 7 and/or distal portions of the lower segment 93 of the sheath 9 to facilitate positioning and/or removal of the inner ring 7.

In various embodiments, the outer ring 5 is more rigid than the inner ring 7. In various embodiments, the outer ring 5 comprises one or more first rings, hoops or segments attached to or embedded within one or more second rings, hoops or segments that are more flexible or less rigid than the first rings, hoops, or segments. In various embodiments, the outer ring 5 is a flexible ring having a lumen therein with a rigid hoop or rod extending within the lumen of the flexible ring, the flexible ring being more flexible than the rigid hoop or rod.

In accordance with various embodiments, the length of the upper segment 91 is predefined or predetermined based upon the expected number of flips that the outer ring 5 is flipped or rolled to gain or maximize retraction. In various embodiments, the predetermined number of flips is about 4 to 6 and in various embodiments is about 5. In various embodiments, as such, the length of the upper segment 91 is about 5 or 4 to 6 times greater than the height or length of the outer ring 5. In various embodiments, the length of the upper segment 91 is at least about 2 times greater than the height or length of the outer ring 5. In accordance with various embodiments, the outer ring 5 is prevented or restricted from being flipped or rolled past the distal end of the upper segment 91 and/or into the lower segment 93 of sheath 9 to maintain ease of use, by one or more barriers or the like, such as a protrusion, bump or raised or different material disposed between the upper and lower segments. In various embodiments, the protrusion, bump or raised or different material extends circumferentially, fully or partially, around the sheath. In various embodiments, the same protrusion is arranged to secure the channel or retainer 31 between the protrusion and the inner ring. In various embodiments, the sheath comprises a separate protrusion, bump or raised or different material arranged to secure the channel or retainer 31 between the protrusion and the inner ring. In various embodiments, the protrusion, bump or raised or different material extends circumferentially, fully or partially, around the sheath. In various embodiments, the protrusion, bump or raised or different material has a width or height smaller than a width or height of the inner ring. In various embodiments, one or more markings or similar identifiers is provided to indicate or delineate the upper segment 91 from the lower segment 93 to further facilitate ease of use of the retractor. In various embodiments, the outer ring is prevented from being rotated, rolled and/or adjusted passed a predetermined stop position between the upper and lower segments of the sheath. In various embodiments, the sheath comprises an indicator marking the predetermined stop position between the upper and lower segments of the sheath for the outer ring or a predetermined position between the upper and lower segments of the sheath. In various embodiments, the length of the upper segment 91 is sufficiently long to provide sufficient slack for insertion of the retractor. In various embodiments, the length of the upper segment 91 is minimized to avoid excessive flipping or rolling of the outer ring 5 causing unwanted operational difficulties.

In various embodiments, the length of the lower segment 93 is predefined or predetermined based on the surgical application. In various embodiments, the length of the lower segment 93 is the expected or predefined final length between the inner and outer rings once the retractor deployed and fully retracted. In various embodiments, the length of the lower segment 93 is approximately the length of a vaginal canal, the thickness of the abdominal wall, and/or any combination therebetween. In various embodiments, the length of the lower segment 93 is longer than the length of the upper segment 91. In various embodiments, the length of the upper segment 91 is less than half the overall or entire length of the sheath 9.

In various embodiments, the outer ring 5 and the inner ring 7 are made of the same material while the sheath 9 is made of a different material. In various embodiments, the outer ring 5 is more rigid or less flexible than the sheath 9 and the sheath 9 is more flexible or less rigid than the inner ring 7. In various embodiments, the upper and lower segments of the sheath 9 are made of the same material and in various embodiments are monolithic or monolithically formed to provide a single, one-piece, or monolithic structure. In various embodiments, the upper segment 91 is made of a more flexible material than the lower segment 93 and/or the lower segment 93 is reinforced or made of a material different or more durable/puncture resistant compared to that of the upper segment 91.

In various embodiments, another or second sheath, membrane or film is disposed between the channel or retainer 31 and the patient's tissue and as such, the retainer is disposed between the other or second sheath and the sheath 9. In various embodiments, the other or second sheath is attached to the sheath 9, the outer ring or is attached to another or different retractor.

In various embodiments, the sheath 9 is arranged to secure the channel or retainer 31 between the lower segment 93 of the sheath and the inner ring 7. In various embodiments, the upper segment 91 has an adjustable length arranged to secure the retainer 31 between the lower segment 93 of the sheath and the inner ring 7. In various embodiments, the sheath comprises a protrusion arranged to secure the retainer 31 between the protrusion and the inner ring 7. In various embodiments, the protrusion extends circumferentially, fully or partially, around the sheath. In various embodiments, the protrusion has a width or height smaller than a width or height of the inner ring 7. In various embodiments, the circumferential retractor comprises a containment bag. In various embodiments, the sheath has a cylindrical shape, a containment bag, and/or a truncated conical shape.

In accordance with various embodiments, the surgical site opening, orifice, or incision is retracted by compressing the inner ring 7 through the opening such that the ring anchors under or within the desired tissue. The inner ring 7, in various embodiments, is arranged to flexible and/or compressible to fit through the opening, and rigid and/or biased to return and holds its original shape once deployed, providing an anchor for the retractor. The outer ring 5 is flipped or rolled downward or towards the inner ring 7 and around itself, gathering up the upper segment 91 of the retractor to retract the opening, i.e., increase the diameter of the patient's opening and thereby providing an access channel through the sheath 9 and the opening. Flipping or rolling down the outer ring 5 increases tension on the sheath 9 and applies circumferential outward pressure on the opening to retract the opening and/or the body wall.

In various embodiments, a sealing or gel cap or port may be attached to the outer ring 5 and/or the patient's body cavity or surgical area insufflated. Instruments may be inserted through the cap, port or sleeves placed or provided in the cap to access the interior anatomy or surgical area during insufflation.

In various embodiments, the outer diameter or periphery of the retractor in operation and/or, as deployed, is delimited or is no larger than the outer diameter of the outer ring 5. In various embodiments, the upper and lower segment sheath allows for surgery through a relatively large instrument port or entry providing optimal or maximized instrument triangulation and through a relatively small incision, without sacrificing the range and amount of retraction or the ease of use. In various embodiments, the retractor provides a retraction diameter of about 25 mm. In various embodiments, the retractor provides a retraction diameter that is larger than a retraction diameter of a similarly sized retractor having a fully cylindrical sheath and/or a fully taper sheath with a similarly sized inner ring. In various embodiments, the retractor provides access or a channel or pathway into a patient's body cavity. In various embodiments, the retractor is adjustable in length to accommodate different patient anatomies and/or 360 degrees of hands-free protection and/or retraction of the opening in the patient. In various embodiments, the retractor may not include an outer ring 5, an inner ring 7 or both. In various embodiments, the retractor comprises a containment bag. In various embodiments, the retractor is usable in open and laparoscopic surgeries. In accordance with various embodiments, the retractor is arranged to provide variable, atraumatic, circumferential retraction of the surgical site. Circumferential retraction of the surgical site increases visibility and access of the target tissue while protecting the opening, channel, or wound margin.

In various embodiments, the sheath 3 is formed die cutting two flat sheets of film, each of which provides of a square or rectangular section and a trapezoidal section. The two cut sheets are connected, e.g., welded together on the side edges, forming an upper cylindrical segment 91 and a lower frustoconical segment 93. In accordance with various embodiments, the sheath is made of a thermoplastic polyurethane (TPU). In various embodiments, the inner and/or outer rings are made of TPU and in various embodiments, the outer ring 5 includes one or more rigid hoops or segments made of, for example, stainless steel, polycarbonate, GRIVORY or the like, connected, embedded, or otherwise attached thereto. The inner ring 7, which is placed through the opening or incision or internal within the patient is smaller than that of the outer ring 5, which remains outside of the opening or incision or external or outside the patient.

In accordance with various embodiments, a channel or retainer 31 is provided to be inserted into and through a patient's body opening, e.g., incision and/or natural orifice. In various embodiments, the channel or retainer 31 has a proximal funnel or taper section and an opposing distal funnel or taper section. In various embodiments, the proximal funnel section from its proximal end has a progressively decreasing diameter to its distal end. In various embodiments, the distal funnel section from its proximal end has a progressively increasing diameter to its distal end. In various embodiments, the channel or retainer 31 has an hourglass shape and in various embodiments, the channel or retainer defines a lumen or access channel or pathway from its proximal end to its distal end. Upon insertion, a distal section of the channel or retainer 31 is disposed internally or inside the surgical space or body cavity, e.g., the vaginal canal, while a proximal section remains outside or external to the surgical space or body cavity.

In various embodiments, the channel or retainer 31 is symmetrical in the axial direction. In various embodiments, the channel or retainer 31 being symmetrical adds to user convenience as placement is non-directional. In various embodiments, the proximal section and the distal section have the same curvature or share the same curve. In various embodiments, the proximal section has a proximal diameter equal to a distal diameter of the distal section. In various embodiments, the proximal section has a distal diameter equal to a proximal diameter of the distal section. In various embodiments, the proximal section has a proximal lip or flange at its proximal end to facilitate or further secure the proximal section to the outside or outer portion of the patient's body and/or the distal section has a distal lip or flange at its distal end to facilitate or further secure the distal section to the inside or inner portion of the patient's body.

In various embodiments, the proximal section and/or proximal lip has a larger diameter, footprint, or profile than the distal section and/or distal lip. In various embodiments, the larger proximal section relative to the distal section facilitates in sealing on the exterior of the patient's body. In various embodiments, the distal section and/or distal lip has a larger diameter, footprint, or profile than the proximal section and/or proximal lip. In various embodiments, a larger distal section relative to the proximal section facilitates or enhances anchoring of the channel or retainer 31 within the body, such as within the vaginal introitus. However, in various embodiments, a larger distal section relative to the proximal section may be difficult to insert and/or through the patient's opening.

In various embodiments, the outermost diameter of the channel or retainer 31 is sized such that it can be placed into the patient's opening, incision, or orifice and provide an initial retraction of the opening. In accordance with various embodiments, the outermost diameter of the channel or retainer 31 is sized to be placed into the vaginal introitus or vaginal canal opening. In various embodiments, the outermost diameter of the channel or retainer 31 is about 45-75 mm and in various embodiments, the innermost diameter is about 20-50 mm.

The innermost diameter of the channel or retainer 31, in various embodiments, can impact the ability of the user to insert an inner ring of a retractor and ultimately the ability to insert and manipulate instruments for the intended procedure. In various embodiments, due to varying anatomy, channels can be provided in multiple sizes and used at the surgeon's discretion. In various embodiments, the channels are provided with different depths while the inner and outer diameters remain the same.

In various embodiments, the depth and/or length of the channel or retainer 31 is such that it is sufficient to grasp or otherwise engage with the tissue structures at the patient's opening, e.g., vaginal introitus, and, in various embodiments, acts as an anchor for placement of the inner ring. In various embodiments, the depth of the channel or retainer 31 is about 20-40 mm and in various embodiments, is about 30 mm. In various embodiments, the depth of the channel or retainer 31 is sized and arranged to extend the thickness of a body wall or entry, e.g., vaginal introitus. In various embodiments, the curvature and/or the depth of the channel or retainer 31 facilitates in secure placement in the body wall or entry, e.g., vaginal introitus.

In accordance with various embodiments, the channel or retainer 31 is made of a semi-rigid polymer material, e.g., KRATON. In various embodiments, the channel or retainer 31 is substantially flexible allowing for manual compression and manipulation to be placed by hand into and through the body opening, e.g., the vaginal introitus. In various embodiments, the channel or retainer 31 is flexible and elastic to rebound to its original or initial shape or un-collapsed or undeformed condition after being released from compression or manual manipulation. In various embodiments, the channel or retainer 31 is arranged to be able to compression, but not adjustable axially, lengthwise, radially and/or having a non-adjustable diameter to facilitate or provide optimal atraumatic friction with the target contact anatomy to further aid in self-fixation of the channel or retainer 31 within the anatomy and/or to the sheath and/or to maximize the surgical operating and viewing space. In various embodiments, the channel or retainer 31 is arranged or is made of a material to facilitate or provide optimal atraumatic friction with the target contact anatomy to further aid in self-fixation of the channel or retainer 31 within the anatomy and/or to the sheath. In various embodiments, the channel or retainer 31 is made of silicone rubber.

In various embodiments, the proximal lip and the distal lip are made of the same material while the rest of the channel or retainer is made of a different material. In various embodiments, the proximal lip is more rigid or less flexible than the rest of the channel or retainer and in various embodiments, the distal lip is more rigid or less flexible than the rest of the channel or retainer. In various embodiments, the proximal lip is more rigid or less flexible than the distal lip. In various embodiments, the proximal and distal sections, with or without the proximal and/or distal lips, are made of the same material and in various embodiments are monolithic or monolithically formed to provide a single, one-piece, or monolithic structure. In various embodiments, the proximal section is made of a more flexible material than the distal section and/or the distal section is reinforced or made of a material different or more durable/puncture resistant compared to that of the proximal section.

In accordance with various embodiments, after initial insertion of the channel or retainer 31 into the body cavity or through the body opening, e.g., vaginal introitus, the channel or retainer 31 provides an initial retraction of the body cavity, e.g., vaginal canal. In various embodiments, the inner ring of the sheath is compressed or otherwise deformed and inserted through the channel or retainer 31. In various embodiments, upward or pulling of the proximal portion of the sheath or outer ring facilitates seating or positioning of the inner ring and/or an upper surface of the inner ring against the channel or retainer 31 and/or a lower surface of the channel or retainer 31, which acts as an anchor point for the sheath to remain or further secure or be affixed in place within the body cavity, e.g., vaginal canal. In various embodiments, a tether 21 is arranged to move the inner ring 7 away from a distal end of a retainer towards a central opening of the retainer as the tether 21 is moved proximally, facilitating removal of the inner ring and/or the retractor.

In various embodiments, the outer ring is flipped, rotated, or rolled gathering or wrapping up the sheath, e.g., an upper segment of the sheath. In various embodiments, the outer ring being flipped or rolled gathering up the sheath, e.g., an upper segment of the sheath, retracts the channel or retainer 31 or enlarges the innermost diameter or central opening of the channel or retainer 31 and/or retracts the body opening, e.g., vaginal introitus, and/or collapses or compresses the curved or parabolic cross-section of the channel or retainer 31 at the patient's opening, e.g., vaginal introitus. The parabolic or curved "pinching-effect" with the channel or retainer 31 facilitates in or provides self-retaining retraction and enhanced sealing capabilities during insufflation of the surgical space. In various embodiments, the sheath is arranged to straighten or flatten out the retainer. In various embodiments, the sheath is arranged to straighten or flatten out a middle portion of the hourglass shape of the retainer. In various embodiments, the sheath is arranged to deform the shape of the retainer, e.g., an hourglass shape, to a different shape, e.g., a cylindrical shape. In various embodiments, the sheath is arranged to straighten, flatten and/or deform the retainer when and/or due to shortening and/or adjusting the length of the upper segment of the sheath and/or wrapping up the upper segment of the sheath around the rotated outer ring. In various embodiments, the channel or retainer 31 does not provide any sealing capabilities or abilities to seal, i.e., is unable to seal, against an instrument inserted through the lumen of the channel or retainer 31. In various embodiments, the channel or retainer 31, for example, comprises of materials, coatings or the like, dimensional sizes or shapes of the lumen, overall sizes or shapes or any combination thereof, that prevents any sealing capabilities or abilities to seal, i.e., is unable to seal, against an instrument inserted through the lumen of the channel or retainer 31. In various embodiments, the retractor does not provide any sealing capabilities or abilities to seal, i.e., is unable to seal, against an instrument inserted through the lumen or access channel through the retractor. In various embodiments, the retractor and channel or retainer together provide retraction of body opening, e.g., vaginal introitus. In various embodiments, retraction or enlargement of the entire body cavity, e.g., vaginal canal, is achieved through insufflation and in which the retractor and/or channel or retainer facilitate or enhance the sealing thereof.

In various embodiments, the inner ring 7 of the retractor 3 and/or inner flange or distal section of the channel or retainer is placed and deployed around the cervix and through a circumferential colpotomy. In various embodiments, the lower segment of the retractor and/or distal section of the channel or retainer is arranged to extend through a patient's vaginal canal and/or into a colpotomy incision. In various embodiments, the length of the lower segment of the retractor and/or distal section of the channel or retainer is at least 3 inches (7.5 centimeters). In various embodiments, the length of the lower segment of the retractor and/or distal section of the channel or retainer is equal or greater than the length of an averaged sized vaginal canal or, in various embodiments, the length of an averaged sized vaginal canal plus the length of a colpotomy incision. The overall width or diameter of the retractor and/or channel or retainer is configured to provide retraction and/or visualization of the vaginal canal, while still being insertable into the colpotomy. In various embodiments, the channel or retainer does not have mechanisms, e.g., bellows, ratchets, hooks, tethers, protrusions/divots or the like, arranged to adjust the channel or retainer axially, lengthwise, radially, and/or along any dimension of the retainer to facilitate or provide optimal atraumatic friction with the target contact anatomy to further aid in self-fixation of the channel or retainer within the anatomy and/or to the sheath and/or to maximize the surgical operating and viewing space.

In accordance with various embodiments, a circumferential retractor system is provided and comprises a first circumferential retractor, a channel or retainer 31 and/or a second circumferential retractor. In various embodiments, the channel or retainer 31 is disposed between the first circumferential retractor and the second circumferential retractor. In various embodiments, the second circumferential retractor is identical to the first circumferential retractor. In various embodiments, the second circumferential retractor comprises a sheath having a cylindrical shape and/or a truncated conical shape. In various embodiments, the second circumferential retractor only has a cylindrical and/or truncated conical shape. In various embodiments, the second circumferential retractor comprises and/or is a containment bag. In various embodiments, the second circumferential retractor has a portion, e.g., a distal portion, arranged to be inserted through and positioned within a body wall, the retainer 31 being arranged to be inserted through and positioned within the body wall and on top of the portion, e.g., the distal portion, of the second circumferential retractor, and/or the lower segment 93 of the first circumferential retractor arranged to be inserted through and positioned within the body wall and on top of the retainer 31.

The above description is provided to enable any person skilled in the art to make and use the devices or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although this application discloses certain embodiments, aspects, and examples, it will be understood by those skilled in the art that the present inventions extend beyond the specifically disclosed embodiments, aspects, and examples to other alternative embodiments and/or uses of the invention and obvious modifications and equivalents thereof. Further, the various features of these inventions can be used alone, or in combination with other features of these inventions other than as expressly described above. It is therefore to be understood that the present invention may be practiced otherwise than specifically described, including various changes in the size, shape, and materials, without departing from the scope of the present invention. Thus, embodiments of the present invention should be considered in all respects as illustrative and not restrictive. Hence, it is intended that the scope of the present inventions herein disclosed should not be limited by the particular disclosed embodiments described above but should be determined only by a fair reading of the claims which follow.

The invention claimed is:

1. A circumferential retractor system comprising:
   a circumferential retractor comprising:
      an outer ring having an outer diameter and arranged to be placed outside of a body cavity;
      an inner ring having an outer diameter and arranged to be placed inside of the body cavity; and
      a sheath comprising:
         an upper segment connected to the outer ring, the upper segment having a cylindrical shape with a proximal end having an inner diameter matching the outer diameter of the outer ring and a distal end having an inner diameter matching the outer diameter of the outer ring, the outer ring being inseparable from the upper segment; and
         a lower segment connected to the inner ring, the lower segment having a frustoconical shape with a proximal end having an inner diameter matching the outer diameter of the outer ring and a distal end having an inner diameter smaller than the outer diameter of the inner ring and smaller than the outer diameter of the outer ring, the sheath delimiting an access channel extending from the outer ring to the inner ring and the upper and lower segments being formed as a monolithic structure and having differing lengths; and
   a monolithic hourglass shaped retainer, the retainer being positioned outside of the access channel, arranged to surround and be in contact with a distal portion of the lower segment of the sheath, and disposed between the upper segment and the inner ring, the sheath being arranged to enlarge a central opening of the retainer and straighten a middle portion of the hourglass shape of the retainer.

2. The system of claim 1 wherein the retainer is arranged to surround only the lower segment of the sheath, and wherein an outer surface of the lower segment of the sheath is disposed between an inner surface of the lower segment and an inner surface of the retainer.

3. The system of claim 2 wherein the proximal end of the upper segment of the sheath is arranged to be placed outside the body cavity and the distal end of the upper segment of the sheath is arranged to be placed inside the body cavity and a length of the upper segment is adjustable, a length of the lower segment is not adjustable, and the lower segment connected to the inner ring is not separable from the inner ring.

4. The system of claim 3 wherein the retainer has a length less than an overall length of the sheath, is compressible, and has a non-adjustable length, the retainer being arranged to be placed between the sheath and tissue, and the lower segment of the sheath conforming to the hourglass shape of the retainer and being arranged to be placed between the retainer and inserted instruments.

5. The system of claim 4 wherein the retainer is more flexible than the outer ring and the inner ring and is less flexible than the sheath, the retainer having an upper inner diameter and a middle inner diameter, the upper inner diameter of the retainer being smaller than an inner diameter of the outer ring; and the middle inner diameter of the retainer being smaller than the upper inner diameter of the retainer and being smaller than an inner diameter of the inner ring.

6. The system of claim 5 wherein the retainer is temporarily deformable by a user, the retainer being deformable from the hourglass shape and biased to return to the hourglass shape.

7. The system of claim 6 wherein the outer ring comprises a flexible ring having a lumen and a curved rod disposed within the lumen of the flexible ring, the curved rod being more rigid than the flexible ring and wherein the outer ring is rotatable about itself.

8. The system of claim 7 wherein a length of the lower segment is longer than a length of the upper segment, the length of the upper segment being less than half an overall length of the sheath and the length of the lower segment being greater than half the overall length of the sheath; wherein the lower segment has an upper inner diameter proximal to the upper segment and a lower inner diameter proximal to the inner ring, the lower inner diameter of the lower segment being smaller than the upper inner diameter of the lower segment; and wherein the outer diameter of the outer ring is greater than the outer diameter of the inner ring.

9. The system of claim 8 wherein the retainer has a distal section having a distal lip at a distal end of the retainer to facilitate securement of the distal section to the inside of the body cavity, and a proximal section having a proximal lip at a proximal end of the retainer to facilitate securement of the proximal section to the outside of the body cavity.

10. The system of claim 9 wherein the distal section of the retainer has an outer diameter greater than the outer diameter of the inner ring; wherein the proximal section of the retainer has an inner diameter greater than the outer diameter of the inner ring; and wherein an inner diameter of the retainer between the proximal section and the distal section of the retainer is smaller than the inner diameter of the inner ring.

11. The system of claim 10 further comprising a sealing cap arranged to connect to the outer ring and portions of the upper segment of the sheath, the sealing cap sealing the access channel and a connection between the sealing cap, the outer ring, and a portion of the upper segment.

12. A circumferential retractor system comprising:
    a circumferential retractor comprising:
       an outer ring having an outer diameter and arranged to be placed outside of a body cavity;
       an inner ring having an outer diameter and arranged to be placed inside of the body cavity; and a sheath comprising:
    an upper segment connected to the outer ring, the upper segment having a cylindrical shape with a proximal end having an outer diameter equal or greater than an inner diameter of the outer ring but less than or equal to the outer diameter of the outer ring and a distal end having an outer diameter equal to the outer diameter of the proximal end of the upper segment, the outer ring being unable to separate from the upper segment; and
    a lower segment connected to and unable to separate from the inner ring, the lower segment having a frustoconical shape with a proximal end having an outer diameter equal to the outer diameter of the proximal end of the upper segment and a distal end having an inner diameter equal to or smaller than the outer diameter of the inner ring and smaller than the outer diameter of the outer ring, the sheath having a lumen extending from the upper segment through the lower segment and delimiting an access channel extending through the lumen from the outer ring to the inner ring, and the upper and lower segments being formed as a monolithic structure and having differing lengths from each other; and
    a monolithic hourglass shaped retainer, the retainer being positioned outside of the access channel and the lumen of the sheath, arranged to surround and be in contact with the lower segment of the sheath, and disposed between the upper segment and the inner ring; and wherein an outer surface of the lower segment of the sheath is disposed between an inner surface of the lower segment and an inner surface of the retainer, the inner ring being arranged to be inserted through a central opening of the retainer and positioned near a distal end of the retainer and the sheath being arranged to enlarge the central opening of the retainer.

13. The system of claim 12 wherein the retainer has a non-adjustable length greater than a length of the upper segment and less than an overall length of the sheath; and wherein the retainer is deformable by a user into a shape different from its hourglass shape, biased to return to its hourglass shape, and arranged to be placed between the sheath and tissue.

14. The system of claim 13 wherein the upper segment of the sheath has a proximal portion arranged to be placed outside a body wall and a distal portion arranged to be placed inside the body wall; and wherein the inner ring is deformable, the outer ring is not deformable and the inner ring is a distalmost portion of the circumferential retractor.

15. The system of claim 14 further comprising a sealing cap arranged to connect to the outer ring and proximal portions of the upper segment of the sheath, a tether attached to the inner ring, and a tether tag attached to the tether, the tether having a length greater than an overall length of the sheath and arranged to move the inner ring away from a distal end of the retainer towards the central opening of the retainer as the tether is moved proximally.

16. The system of claim 15 further comprising a containment bag having a distal portion arranged to be inserted through the body wall and positioned within the body cavity, the retainer being arranged to be inserted through the body wall and positioned on top of the containment bag, and the lower segment of the circumferential retractor arranged to be inserted through the body wall and positioned on top of the retainer.

17. The system of claim 16 wherein the retainer is more rigid than the upper segment and the lower segment of the sheath, the upper segment of the sheath having an adjustable length, the retainer having a fixed length, and the lower segment having a fixed and non-adjustable length, the sheath being arranged to secure the retainer between the lower segment of the sheath and the inner ring.

18. The system of claim 17 wherein the outer ring comprises a flexible ring having a lumen and a curved rod disposed within the lumen of the flexible ring, the curved rod being more rigid than the flexible ring and the inner ring and wherein the outer ring is rotatable about itself.

19. The system of claim 17 wherein the retainer has a distal section having a distal lip at the distal end of the retainer to facilitate securement of the distal section of the retainer to the inside of the body cavity and the inner ring; and the retainer has a proximal section having a proximal lip at a proximal end of the retainer to facilitate securement of the proximal section to the outside of the body cavity.

20. The system of claim 15 further comprising a second circumferential retractor having a distal portion arranged to be inserted through the body wall and positioned within the body cavity, the retainer being arranged to be inserted through the body wall and positioned on top of the second circumferential retractor, and the lower segment of the circumferential retractor arranged to be inserted through the body wall and positioned on top of the retainer.

* * * * *